US012734336B2

(12) United States Patent
Leo

(10) Patent No.: US 12,734,336 B2

(45) Date of Patent: Sep. 15, 2026

(54) ELONGATED SURGICAL MANIPULATOR WITH BODY POSITION AND DISTAL FORCE SENSING

(71) Applicant: St. Jude Medical International Holding S.á.r.l., Luxembourg (LU)

(72) Inventor: Giovanni Leo, Cologny (CH)

(73) Assignee: ST JUDE MEDICAL INTERNATIONAL HOLDING S.À R.L., Luxembourg (LU)

( * ) Notice: Subject to any disclaimer, the term of this patent is extended or adjusted under 35 U.S.C. 154(b) by 1019 days.

(21) Appl. No.: 17/155,968

(22) Filed: Jan. 22, 2021

(65) Prior Publication Data

US 2021/0138198 A1 May 13, 2021

Related U.S. Application Data

(60) Continuation of application No. 15/978,993, filed on May 14, 2018, now Pat. No. 10,905,855, which is a (Continued)

(51) Int. Cl.
*A61M 25/01* (2006.01)
*A61B 5/00* (2006.01)
(Continued)

(52) U.S. Cl.
CPC ....... *A61M 25/0158* (2013.01); *A61B 5/0084* (2013.01); *A61B 5/6843* (2013.01); (Continued)

(58) Field of Classification Search
CPC ............. A61M 25/0158; A61B 5/0084; A61B 5/6843; A61B 34/30; A61B 34/70; A61B 5/01; A61B 1/009
See application file for complete search history.

(56) References Cited

U.S. PATENT DOCUMENTS 4,757,194 A 7/1988 Simms
4,918,492 A 4/1990 Ferdinand et al.
(Continued)

FOREIGN PATENT DOCUMENTS

DE 3020785 A1 12/1981
DE 3828550 A1 3/1990
(Continued)

OTHER PUBLICATIONS

Calkins, et al., "HRS/EHRA/ECAS Expert Consensus Statement on Catheter and Surgical Ablation of Atrial Fibrillation: Recommendations of Personnel, Policy, Procedures and Follow-up", Eurospace (2007) 9, 335-379.
(Continued)

*Primary Examiner* — Bhisma Mehta
*Assistant Examiner* — Fatimata Sahra Diop
(74) *Attorney, Agent, or Firm* — Dentons Durham Jones Pinegar; Richard Christiansen; Lilly Godfrey

(57) ABSTRACT

An elongated surgical manipulator apparatus and method of operating enables determination of the shape of a flexible portion of the elongated surgical manipulator and/or the location of an arbitrary point thereon, as well as a measure of a contact force exerted on a distal portion of the manipulator. A plurality of fiber optics are operatively coupled with the manipulator, each of the fiber optics including a plurality of fiber Bragg gratings for determination of the shape and/or position. Each of the fiber optics further includes a fiber optic strain gauge such as a Bragg grating or a Fabry-Perot resonator at a distal portion of the elongated surgical manipulator that is isolated from the strain associated with the bending of the manipulator. The fiber optic strain gauges at the distal portion may thus be used to detect a force vector (magnitude and direction) imposed on the distal portion.

15 Claims, 8 Drawing Sheets

Related U.S. Application Data continuation of application No. 14/147,859, filed on Jan. 6, 2014, now Pat. No. 9,993,617, which is a division of application No. 12/127,657, filed on May 27, 2008, now Pat. No. 8,622,935.

(60) Provisional application No. 60/931,762, filed on May 25, 2007.

(51) Int. Cl.
*A61B 34/00* (2016.01)
*A61B 34/30* (2016.01)
*A61B 5/01* (2006.01)

(52) U.S. Cl.
CPC .............. *A61B 34/30* (2016.02); *A61B 34/70* (2016.02); *A61B 5/01* (2013.01)

(56) References Cited

U.S. PATENT DOCUMENTS 4,966,597 A 10/1990 Cosman
4,983,034 A 1/1991 Spillman et al.
5,014,709 A 5/1991 Belkhagen et al.
5,018,529 A 5/1991 Tenerz et al.
5,065,010 A 11/1991 Knute et al.
5,104,392 A 4/1992 Kittrell et al.
5,122,137 A 6/1992 Lennox
5,174,277 A 12/1992 Matsumaru
5,178,153 A 1/1993 Einzig et al.
5,201,317 A 4/1993 Kanazawa et al.
5,202,939 A 4/1993 Belleville et al.
5,279,793 A 1/1994 Glass et al.
5,289,256 A 2/1994 Gramling
5,321,501 A 6/1994 Schuman et al.
5,348,019 A 9/1994 Childers et al.
5,392,117 A 2/1995 Belleville et al.
5,396,887 A 3/1995 Imran
5,409,000 A 4/1995 Imran et al.
5,423,807 A 6/1995 Milder
5,446,546 A 8/1995 Breidenbach et al.
5,575,787 A 11/1996 Abela et al.
5,594,819 A 1/1997 Narendran et al.
5,622,108 A 4/1997 Benedetto et al.
5,633,494 A 5/1997 Danisch et al.
5,645,065 A 7/1997 Shapiro et al.
5,688,267 A 11/1997 Panescu et al.
5,693,043 A 12/1997 Kittrell et al.
5,696,863 A 12/1997 Kleinerman et al.
5,769,847 A 6/1998 Panescu et al.
5,772,590 A 6/1998 Webster
5,782,828 A 7/1998 Chen et al.
5,798,521 A * 8/1998 Froggatt ................ G01B 11/18 250/227.14
5,807,265 A 9/1998 Itoigawa et al.
5,833,688 A 11/1998 Sieben et al.
5,844,927 A 12/1998 Kringlebotn et al.
5,858,717 A 1/1999 Scobey et al.
5,904,658 A 5/1999 Niederauer et al.
5,906,614 A 5/1999 Stern et al.
5,967,978 A 10/1999 Littmann et al.
6,039,743 A 3/2000 Quiachon et al.
6,056,436 A 5/2000 Singh et al.
6,063,078 A 5/2000 Wittkampf
6,066,120 A 5/2000 Gregory et al.
6,088,088 A 7/2000 Fortenberry et al.
6,102,926 A 8/2000 Tartaglia et al.
6,113,590 A 9/2000 Fischer et al.
6,113,593 A 9/2000 Tu et al.
6,120,476 A 9/2000 Fung et al.
6,120,520 A 9/2000 Saadat et al.
6,129,667 A 10/2000 Dumoulin et al.
6,133,593 A 10/2000 Boos et al.
6,134,003 A 10/2000 Tearney et al.
6,171,275 B1 1/2001 Webster et al.
6,173,091 B1 1/2001 Reich et al.
6,175,669 B1 1/2001 Colston et al.
6,197,023 B1 3/2001 Muntermann et al.
6,210,346 B1 4/2001 Hall
6,217,574 B1 4/2001 Webster et al.
6,226,542 B1 5/2001 Reisfeld et al.
6,246,898 B1 6/2001 Vesely et al.
6,256,090 B1 * 7/2001 Chen .................... G01V 1/3835 356/73.1
6,262,822 B1 7/2001 Obhi et al.
6,266,542 B1 7/2001 Stern et al.
6,266,551 B1 7/2001 Osadchy et al.
6,272,371 B1 8/2001 Shlomo et al.
6,276,215 B1 8/2001 Berg et al.
6,310,990 B1 10/2001 Bellemore et al.
6,324,918 B1 12/2001 Gitis et al.
6,370,412 B1 4/2002 Armoundas et al.
6,398,778 B1 6/2002 Gu et al.
6,425,894 B1 7/2002 Brucker et al.
6,451,009 B1 9/2002 Dasilva et al.
6,458,123 B1 10/2002 Brucker
6,466,811 B1 10/2002 Hassett et al.
6,470,205 B2 10/2002 Bosselmann et al.
6,470,286 B1 10/2002 Watts et al.
6,471,710 B1 10/2002 Bucholtz et al.
6,546,271 B1 4/2003 Reisfeld et al.
6,547,780 B1 4/2003 Sinofsky et al.
6,558,378 B2 5/2003 Sherman et al.
6,563,970 B1 5/2003 Bohnert et al.
6,572,804 B2 6/2003 Randall et al.
6,602,242 B1 8/2003 Fung et al.
6,660,001 B2 12/2003 Gregory et al.
6,674,928 B2 1/2004 Johnson et al.
6,695,808 B2 2/2004 Tom
6,701,931 B2 3/2004 Sliwa et al.
6,852,109 B2 2/2005 Winston et al.
6,868,195 B2 3/2005 Fujita et al.
6,898,338 B2 5/2005 Kersey et al.
6,915,048 B2 7/2005 Kersey et al.
6,947,637 B2 9/2005 Smith et al.
6,955,675 B2 10/2005 Jain et al.
6,986,769 B2 1/2006 Nelson et al.
7,050,662 B2 5/2006 Behrmann et al.
7,114,938 B2 10/2006 Chou et al.
7,173,713 B2 2/2007 Xu et al.
7,241,986 B2 7/2007 Wang et al.
7,460,964 B2 12/2008 Mizota et al.
7,466,879 B2 12/2008 Tjin et al.
7,491,957 B2 2/2009 Kitamura et al.
7,903,907 B1 3/2011 Park et al.
8,048,063 B2 11/2011 Aeby et al.
8,075,498 B2 12/2011 Leo et al.
8,157,789 B2 4/2012 Leo et al.
2001/0021843 A1 9/2001 Bosselmann
2002/0041722 A1 4/2002 Johnson et al.
2002/0041723 A1 4/2002 Ronnekleiv
2002/0057859 A1 5/2002 Walter et al.
2002/0072680 A1 6/2002 Schock et al.
2004/0082844 A1 4/2004 Vardi et al.
2004/0165810 A1 * 8/2004 Fujita .................. A61B 1/0055 385/12
2004/0206365 A1 10/2004 Knowlton et al.
2004/0243119 A1 12/2004 Lane et al.
2005/0062979 A1 3/2005 Zhu et al.
2005/0085693 A1 4/2005 Belson et al.
2005/0213870 A1 9/2005 Kersey et al.
2006/0013523 A1 1/2006 Childlers et al.
2006/0045408 A1 3/2006 Jones et al.
2006/0100610 A1 5/2006 Wallace et al.
2006/0133715 A1 6/2006 Belleville et al.
2006/0200049 A1 9/2006 Leo et al.
2006/0263002 A1 11/2006 Pocha et al.
2007/0014490 A1 1/2007 Silverbrook et al.
2007/0041019 A1 2/2007 Schmidt et al.
2007/0043338 A1 2/2007 Moll et al.
2007/0060847 A1 * 3/2007 Leo ..................... A61B 5/0066 600/587
2007/0065077 A1 3/2007 Childers et al.
2007/0151390 A1 7/2007 Blumenkranz et al.

(56) References Cited

U.S. PATENT DOCUMENTS

| | | | | |
|---|---|---|---|---|
| 2007/0151391 | A1 | 7/2007 | Larkin et al. | |
| 2007/0156019 | A1 | 7/2007 | Larkin et al. | |
| 2007/0265503 | A1* | 11/2007 | Schlesinger .......... | A61B 5/065 600/182 |
| 2008/0009750 | A1 | 1/2008 | Aeby et al. | |
| 2008/0294144 | A1 | 11/2008 | Leo et al. | |
| 2009/0138007 | A1 | 5/2009 | Govari et al. | |
| 2009/0177095 | A1 | 7/2009 | Aeby et al. | |
| 2009/0287092 | A1 | 11/2009 | Leo et al. | |
| 2009/0306643 | A1 | 12/2009 | Pappone et al. | |
| 2009/0306650 | A1 | 12/2009 | Govari et al. | |
| 2010/0063478 | A1 | 3/2010 | Selkee et al. | |
| 2010/0087835 | A1 | 4/2010 | Blumenkranz et al. | |
| 2010/0094163 | A1 | 4/2010 | Deladi et al. | |
| 2010/0328675 | A1 | 12/2010 | Bertholds et al. | |
| 2011/0087112 | A1* | 4/2011 | Leo ....................... | A61B 90/98 600/478 |
| 2011/0224684 | A1* | 9/2011 | Larkin .................. | A61B 90/30 29/428 |
| 2012/0078138 | A1 | 3/2012 | Leo et al. | |
| 2012/0132009 | A1 | 5/2012 | Prisco | |
| 2012/0265102 | A1 | 10/2012 | Leo et al. | |
| 2013/0090552 | A1 | 4/2013 | Ramamurthy et al. | |
| 2014/0364848 | A1 | 12/2014 | Heimbecher et al. | |
| 2015/0029511 | A1 | 1/2015 | 'T Hooft et al. | |
| 2016/0334203 | A1 | 11/2016 | Cui et al. | |

FOREIGN PATENT DOCUMENTS

| | | | |
|---|---|---|---|
| EP | 0281405 | | 9/1988 |
| EP | 0934728 | | 8/1999 |
| EP | 1858401 | A1 | 11/2007 |
| EP | 1909650 | A2 | 4/2008 |
| EP | 2047797 | B1 | 4/2014 |
| JP | 09297078 | A | 11/1997 |
| JP | 10137200 | A | 5/1998 |
| JP | 2000227367 | A | 8/2000 |
| JP | 2004251779 | A | 9/2004 |
| WO | 9729678 | A2 | 8/1997 |
| WO | 9732182 | | 9/1997 |
| WO | 9738637 | A1 | 10/1997 |
| WO | 9819044 | A1 | 5/1998 |
| WO | 9945994 | A1 | 9/1999 |
| WO | 0133165 | A1 | 5/2001 |
| WO | 0174252 | A2 | 10/2001 |
| WO | 0219898 | A2 | 3/2002 |
| WO | 0219903 | A1 | 3/2002 |
| WO | 0223148 | A1 | 3/2002 |
| WO | 0247751 | A2 | 6/2002 |
| WO | 2004002303 | A1 | 1/2004 |
| WO | 2005059510 | A2 | 6/2005 |
| WO | 2006092707 | A1 | 9/2006 |
| WO | 2007015139 | A3 | 4/2007 |
| WO | 2007050960 | A2 | 5/2007 |
| WO | 2007111737 | A2 | 10/2007 |
| WO | 2008000246 | A2 | 1/2008 |
| WO | 2008003307 | A2 | 1/2008 |
| WO | 2008045958 | A2 | 4/2008 |
| WO | 2009114955 | A1 | 9/2009 |

OTHER PUBLICATIONS

Cappato, et al., "Worldwide Survey on the Methods, Efficacy, and Safety of Catheter Ablation for Human Atrial Fibrillation", Journal of the American Heart Association, 2005, 7 pgs.
Peirs, et al., "A micro optical force sensor for force feedback during minimally invasive robotic surgery", Sensors and Actuators A 115, 2004, 447-455.
Del Villar, et al., "Optimization of Sensitivity in Long Period Fiber Gratings with Overlay Deposition", Optic Express, vol. 13, No. 1, Jan. 10, 2005, 56-69.
Dickmann, "Experiment 03, Fabry Perot Resonator", 2003, 1-19.
Dupont, "DuPont Zenite LCP liquid crystal polymer resin", Product and Property Guide, K-15415, May 2006. 35 pgs.
Erdemir, et al., "Fiberoptic Measurement of Tendon Forces is Influenced by Skin Movement Artifact", Journal of Biomechanics, vol. 36, No. 3, 449-455, Mar. 2003.
Rao, "Recent progress in applications of in-fibre Bragg grating sensors", Optics and Lasers in Engineering Elseiver UK, vol. 31, No. 4, Apr. 1999, 297-324.
Schmidt, et al., "Fiber-Optic Extrinsic Fabry-Perot Interoferometer Strain Sensor with <50 pm Displacement Resolution Using Three-Wavelength Digital Phase Demodulation", Optic Express, vol. 8, No. 8, Apr. 9, 2001, 475-480.
Shah, et al., "Evaluation of a New Catheter Sensor for Reel-Time Measurement of Tissue Contact", Heart Rhythm Society, vol. 3, Issue 5 (Supplement), S75-576, AB36-6, May 2006, 1 pg.
Van Uffelen, et al. "Anchoring points for fibre optic strain sensors". Optical Techniques for Smart Structures and Structural Monitoring. 1 pg. Feb. 17, 1997.
Xiao, et al. "Fiber optic pressure sensor with self-compensation capability for harsh environment applications". Optical Engineering 44(5), 054-403, XP-002527158. May 2005. 10 pgs.
Fearn, et al., "An Optical Transducer for Single Myofibril Force Measurement", IEEE Transaction on Biomedical Engineering, vol. 40, No. 11, 1993, 1127-1132.
FISO, "FOS-N Strain Sensor", FISO Technologies Inc. Canada, 2006, 2 pgs.
Fuster, et al., "ACC/AHA/ESC 2006 Guidelines for the Management of Patents with Atrial Fibrillation", Circulation Journal of the American Heart Association, 2006, e319-e321.
Hasin, et al., "Miniature Force Transducer for Myocardial Stimulation and Local Tension Measurements", IEEE Transactions on Biomedical Engineering, vol. BME-26, No. 2, Feb. 1979, 104-105.
Inaudi, "Application of optical fiber sensor in civil structural monitoring", Proceedings of the SPIE-The International Society for Optical Engineering SPIE-INT. Soc. Opt. Eng USA, vol. 4328, 2001, 1-10.
Yokoyama, et al. "Novel Radiofrequency Ablation Catheter with Contact Force Sensor Predicts Lesion Size and Incidence of Steam Pop in Canine Model". Heart Rhythm Society, vol. 4, Issue 5 (Supplement), S340-S341, p. 05-106. 1 pg. May 2007.
Zhang, et al. "On SDM/WDM FBG Sensor Net for Shape Detection of Endoscope".Proceedings of the IEEE, International Conference on Mechatronics and Automation, Niagra Falls, Canada. Jul. 2005. pp. 1986-1991.
Meller, "Extrinsic Fabry-Perot Interferometer System Using Wavelength Modulated Source", Dec. 1996, 57 pgs.
Korni, et al., "Optic Fibre as a Transducer of Tendomuscular Forces", European Journal of Applied Physiology and Occupational Physiology, Vo. 72, No. 3, 1996, 278-280.
Brown, "Development of Biollouin Scattering Based Distributed Fiber-Optic Strain Sensor", The University of New Brunswick, 2001. 2 pgs.
Lo, "Using in-fiber Bragg-grating sensors for measuring axial strain and temperature simultaneously on surfaces of structures", Optical Engineering, vol. 37, Aug. 1998, 2272-2276.
Luna Innovations, "EFPI Techniques for Strain and Displacement Sensing", Rec. C, Aug. 1999, 6 pgs.
Luna Innovations, "Fiber Optic Bragg Grating Sensor", www.lunainnovations.com/products/shape.asp, Aug. 2005, 18 pgs.
"Endosense achieves ISO 13485 certification", Aug. 12, 2008, 1 pg.
"Endosense launches TOCCATA clinical study", Multi-center European Safety Study on Groundbreaking Technology for the Treatment of Atrial Arrhythmias, Oct. 7, 2008, 1 pg.
"Endosense receives CE mark for Tacticath force-sensing ablation catheter", May 4, 2009, 1 pg.
"Endosense unveils five groundbreaking abstracts on contact force measurement for catheter ablation", May 13, 2008, 1 pg.
"IntelliSense Fine Force Technology", Hansen Medical (website) http://www.hansenmedical.com/products/intellisense.aspx, Sep. 22, 2009, 1 pg.
Natale, et al., "Venice Chart International Consensus Document on Atrial Fibrillation Ablation", Journal of Cardiovascular Electrophysiology, vol. 18, No. 5, 2007, 560-580.

(56) References Cited

OTHER PUBLICATIONS

Paris-Seely, et al., "A Compliance-Independent Pressure Transducer for Biomedical Device-Tissue Interfacesm", Biomedical Instrumentation & Technology, vol. 34, No. 6, Nov.-Dec. 2000, 423-31.
"Precision Photonics Corporation", Basic Physics and Design of Etalons, 2003, 1-5.
"Sensei X Robotic Catheter System for Electrophysiology Procedures", MedGadget, Sep. 18, 2009, 4 pgs.
"The Unique Force Sensor Ablation Catheter", www.endosense.com/site/product.htm, Mar. 14, 2007, 1 pg.
Barb, et al., "Versatile, High-Speed Force Transducer Using a Laser Diode Beam as an Optical Lever", Journal of Applied Physiology, vol. 88, No. 1, 2000, 308-314.
Barrett, et al., "Extrinsic Fabry-Perot Interometer for Measuring the Stiffness of Ailiary Bundles of Hair Cells", IEEE Transactions on Biomedical Engineering, vol. 46. No. 3, Mar. 1999, 331-339.

* cited by examiner

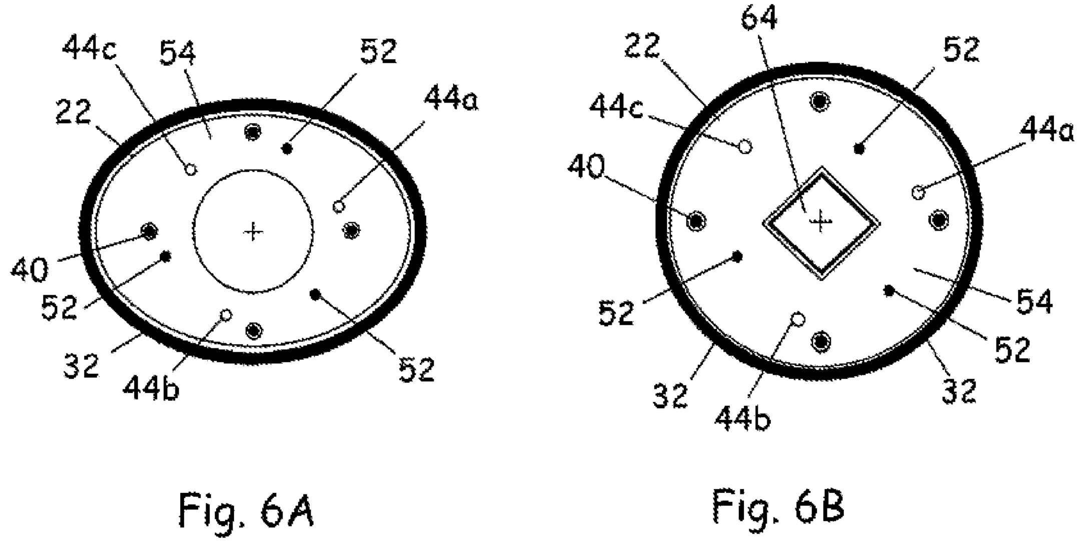
Fig. 6A
Fig. 6B
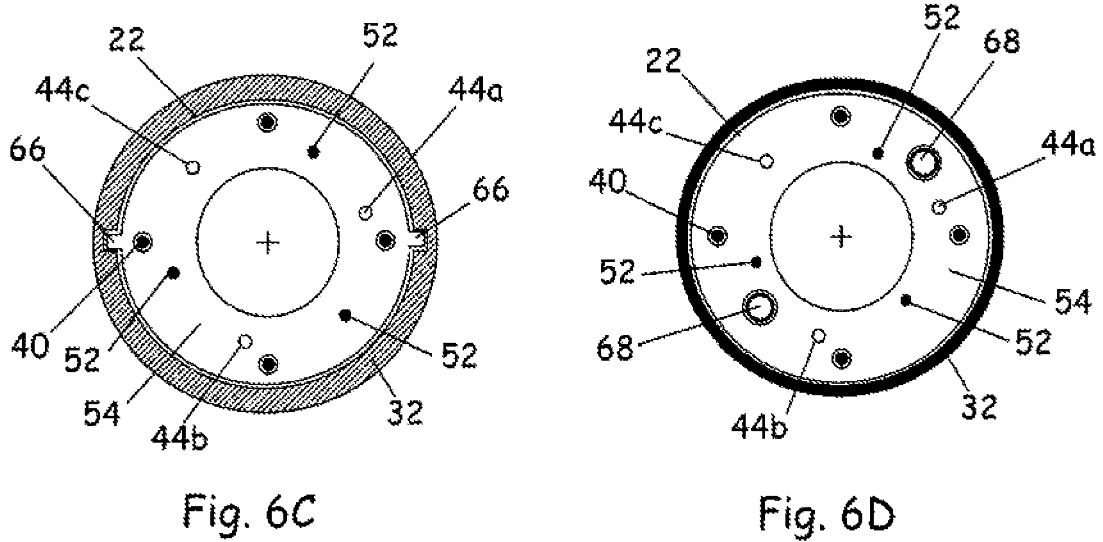
Fig. 6C
Fig. 6D 130
132
(Fig.7C)
x
7B
7B
r, y
152
52
150
152
52

162
52
132
152
110
156
162

F
116
142
110
122
102
118a
130
118b
7A
7A
118c
106
96
100
x
z
θ
r, y
26

114
z
142
116
146
122
110
118a
148
152
112
132, 134
130
106
118b
100
160
140
128
118c
162
26
96
48
144
34
r, y
102
44a
145

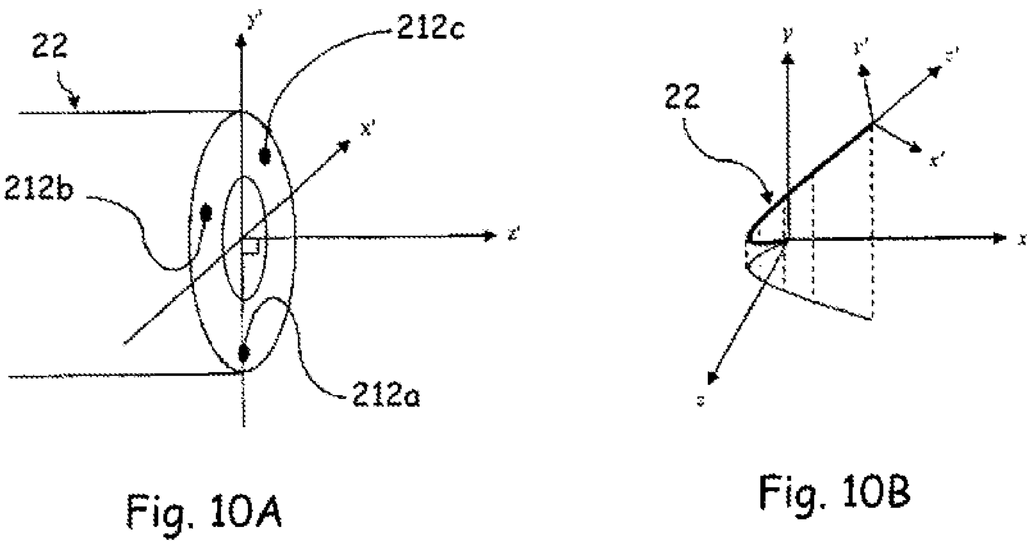
Fig. 10A
Fig. 10B
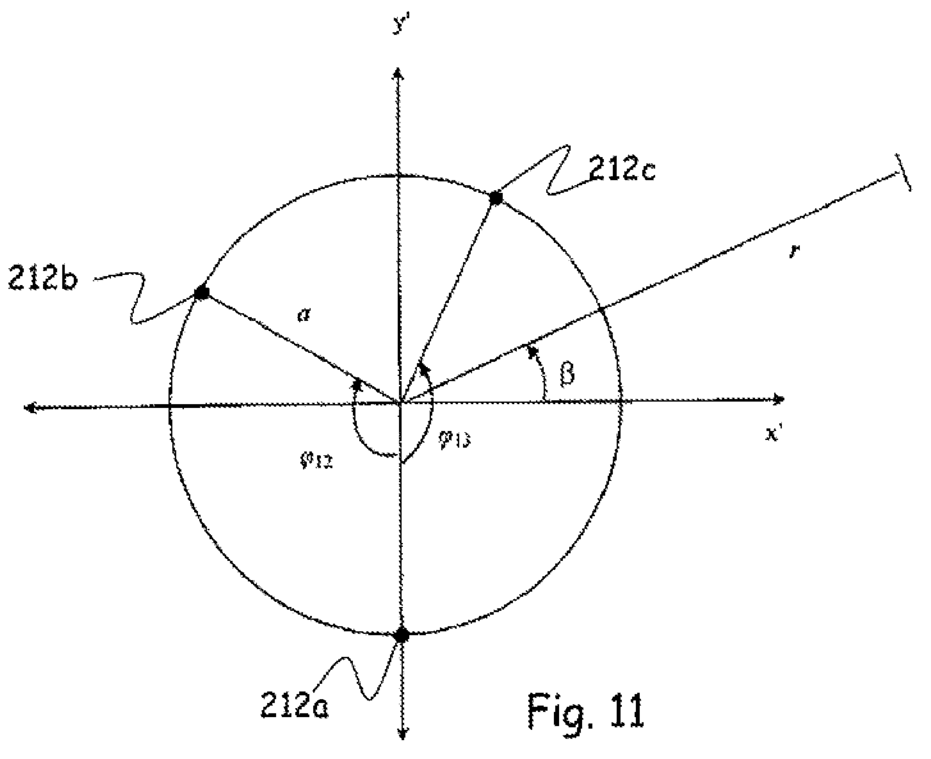
Fig. 11

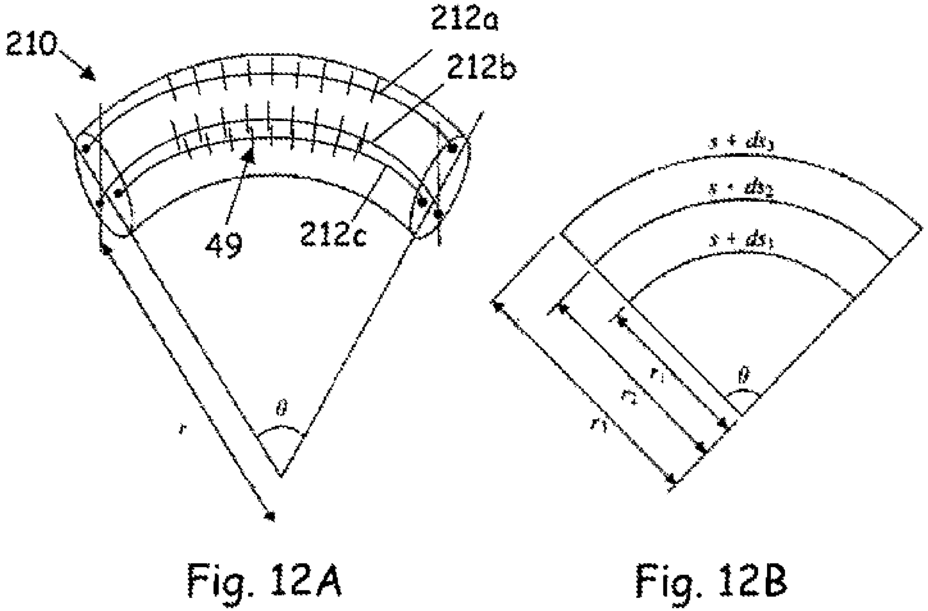
Fig. 12A
Fig. 12B
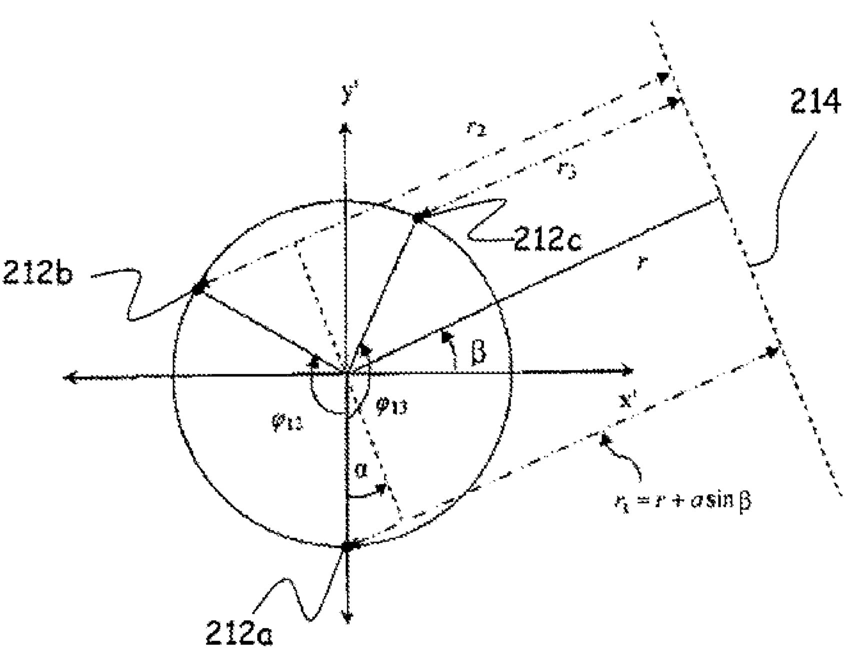
Fig. 13

ELONGATED SURGICAL MANIPULATOR WITH BODY POSITION AND DISTAL FORCE SENSING

RELATED APPLICATIONS

The present application is a continuation of application Ser. No. 15/978,993 filed May 14, 2018, which is a continuation of application Ser. No. 14/147,859 filed Jan. 6, 2014, now U.S. Pat. No. 9,993,617, which is a divisional of application Ser. No. 12/127,657 filed May 27, 2008, now U.S. Pat. No. 8,622,935, which claims the benefit of U.S. Provisional Application No. 60/931,762 filed May 25, 2007, the disclosures of which are hereby incorporated by reference in their entireties. The present application is related to, but does not claim the benefit of, application Ser. No. 11/753,429 filed May 24, 2007 and now issued as 8,157,789, the disclosure of which is incorporated by reference in its entirety.

FIELD OF THE INVENTION

The disclosed invention relates generally to sensing devices capable of resolving the position of an elongated surgical manipulator as well as the magnitude and direction of a force vector externally imposed on a distal portion of the surgical manipulator. More specifically, the invention relates to a manipulator with elongated body shape resolution and a force sensing distal tip to aid in the positioning of catheters used in humans or animals, or for serving as feedback elements in robotic surgical systems.

BACKGROUND OF THE INVENTION

The use of optical fiber strain sensors to detect the reactionary force on the end effector of a catheter is known. U.S. Patent Application Publication No. 2007/0060847 to Leo et al. (Leo I), assigned to the assignee of the present application, discloses an apparatus and method using fiber Bragg gratings coupled to a deformable body for inferring the magnitude and direction of a reaction force imparted on the distal portion of an end effector. U.S. patent application Ser. No. 11/753,429 to Leo et al. (Leo II), also assigned to the assignee of the present application, discloses an apparatus and method using Fabry-Perot resonators operatively coupled to a fiber optic to infer the magnitude and direction of reaction forces imparted on the distal portion of an end effector. While these devices have advanced the art in terms of resolving the forces applied in touch sensitive operations such as ablation procedures, they lack an integrated way of determining the position or location of the catheter during the procedures. Instead, the position of the catheter and/or end effector within a patient must be determined by an alternative approaches such as fluoroscopy or fMRI.

Position sensing and shape resolution using multiple arrays of fiber Bragg gratings is also known for elongated catheter bodies without an end effector. U.S. Patent Application Publication No. 2007/0065077 to Childers et al. (Childers) and U.S. Patent Application Publication No. 2007/0265503 to Schlesinger, et al. (Schlesinger) disclose the use of fiber Bragg gratings operatively coupled to an elongate flexible body to sense the local strains of the body at a multitude of points, and a method for inferring the shape of the body and a position of the distal portion of the elongated catheter body based on the strain imposed on the fiber Bragg gratings.

A system that enables accurate determination of touching forces on a distal portion in combination with simultaneous accurate position sensing of an elongated surgical manipulator would be welcome.

SUMMARY OF THE INVENTION

Various embodiments of the disclosed invention provide effective apparatuses and procedures for resolving shape, position and force sensing of automated or manually controlled elongated surgical manipulators. Certain embodiments include the dual function of position indication of an end effector of the elongated surgical manipulator and the magnitude and direction of a reaction force exerted thereon.

Certain embodiments include a surgical manipulator arm or catheter body having an elongate flexible body that includes one or more fiber optics, each fiber optic being equipped with a number of fiber Bragg gratings. The elongate flexible body may include a flexing portion and a distal portion. In some embodiments, the flexing portion includes a plurality of fiber Bragg gratings and is configured for flexing with a steering mechanism, the operation of which does not flex the distal portion. The distal portion may include fiber optic sensors, such as fiber Bragg gratings or Fabry-Perot resonators, that are isolated from the flexing strain experienced by the flexing portion, and thus are suited for detecting deflection due to reaction forces imposed on the distal portion.

Embodiments of the present invention overcome the problems which would otherwise preclude combining the position sensing teaching of Childers and Schlesinger with the force sensing arrangements disclosed by Leo I or Leo II. Neither Childers nor Schlesinger have an end effector or can provide for an irrigation passage extending through the flexible elongate body. In particular, Schlesinger teaches a catheter having a soft tapered distal tip that is even more plyable than the flexible portion of the manipulator. (See U.S. Patent Application Publication No. 2006/0100610, which Schlesinger incorporates by reference in its entirety.) Such a tip is incompatible with the requirements of a force sensing assembly using fiber optics at the distal portion of an elongated surgical manipulator because the tip will generally flex under its own weight and cause the optical fiber strain sensors to undergo an orientation, non-force related strain. Soft plyable tips are also incompatible with ablation and/or irrigation end effectors.

In various embodiments of the present invention, an electromagnetic source, such as a tunable laser, may be used to interrogate each of the fiber optics. The reflected wavelengths from fiber Bragg gratings corresponding to the flexing portion provides knowledge of the strain of each, from which the shape or geometric configuration of at least a portion of the elongate flexible body may be inferred. The inferred shape may also provide knowledge of the position of the distal extremity of the elongate flexible body.

In another embodiment of the invention, the elongate body may be a catheter having an end effector such as an ablation catheter. The end effector may have a rigid or semi-rigid section that enables a stable reference, for example where the catheter goes through the septum in a left atrium intervention from the femoral vein.

BRIEF DESCRIPTION OF THE DRAWINGS

FIGS. 6A through 6D are enlarged, exemplary cross-sections of the base within a rigid tube member for various embodiments of the invention;

FIGS. 10A and 10B depict a sensor frame coordinate system in an embodiment of the invention;

FIG. 11 depicts a bend parameter schematic in an embodiment of the invention;

FIGS. 12A and 12B depict a bend geometry of an instrumented flexible section in an embodiment of the invention; and FIG. 13 depicts a cross-section of an instrumented flexible section in an embodiment of the invention.

DETAILED DESCRIPTION OF THE DRAWINGS

Figure 1:
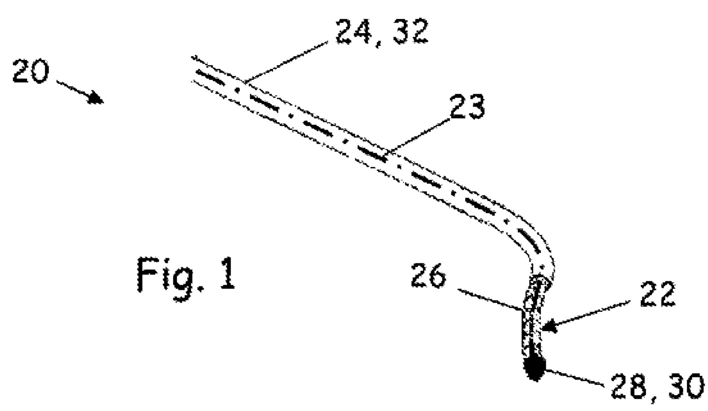
FIG. 1 is a partial perspective view of a manipulator arm in an embodiment of the invention.
Figure 2:
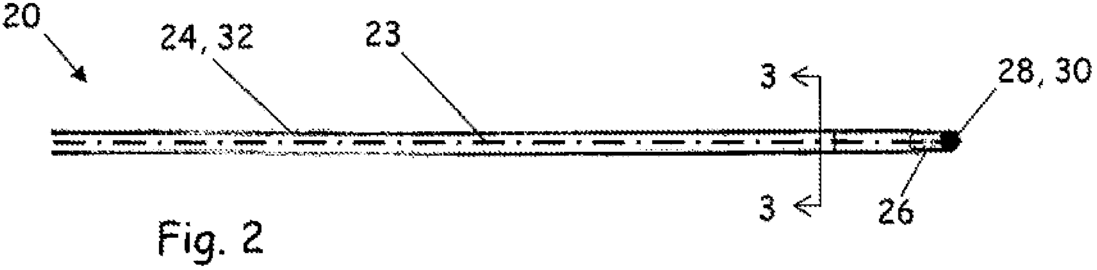
FIG. 2 is a side elevation view of the manipulator arm of FIG. 1.

Referring to FIGS. 1 and 2, a manipulator arm 20 comprising an elongate flexible instrument body 22 is depicted in an embodiment of the invention. The elongate flexible body 22 defines a longitudinal axis 23 that conforms to the shape of and runs the length of the elongate flexible body 22. The elongate flexible body 22 includes a proximal portion 24 and a flexing portion 26. The manipulator arm 20 may further include an end effector 28 that defines a distal portion 30 of the manipulator arm 20.

The proximal portion 24 may be supported by a rigid member 32. In the depicted embodiment, the rigid member 32 is a tubular member that serves as a cladding for the elongate flexible body 22 over the length of the proximal portion 24. The distal portion 30 may include a yoke portion 34 at the interface with the flexing portion 26. The proximal portion 24 may be permanently attached to the rigid member 32, or may be configured to move along the longitudinal axis 23 relative to the rigid member 32. In still other embodiments, the flexing portion 26 is anchored directly to a base without use of a rigid member (not depicted).

Figure 3:
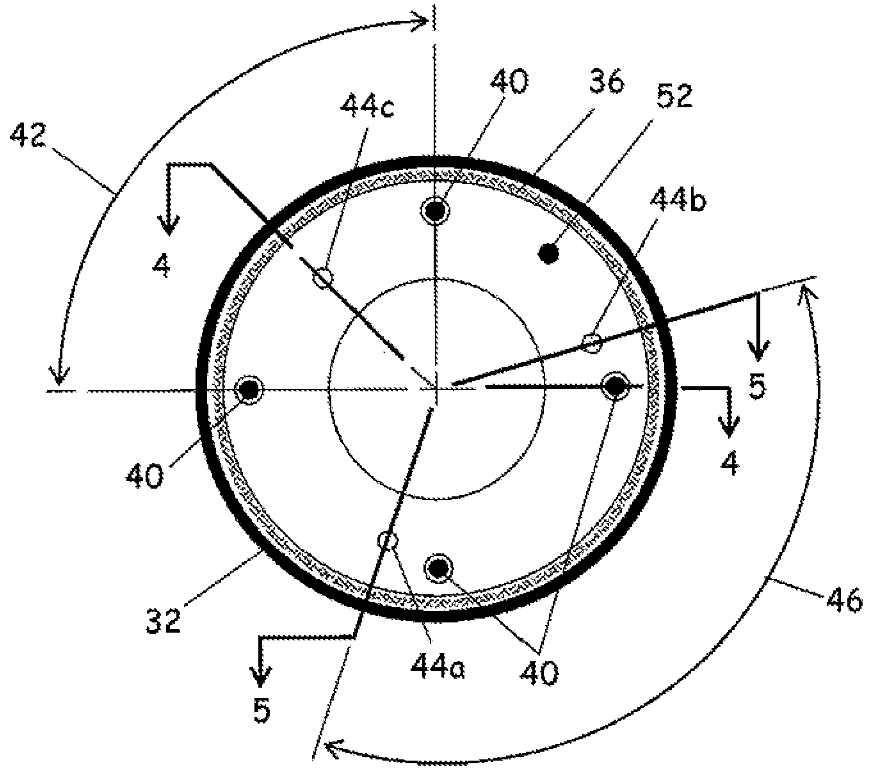
FIG. 3 is an enlarged sectional view of the manipulator arm of FIG. 2.
Figures 4, 5:
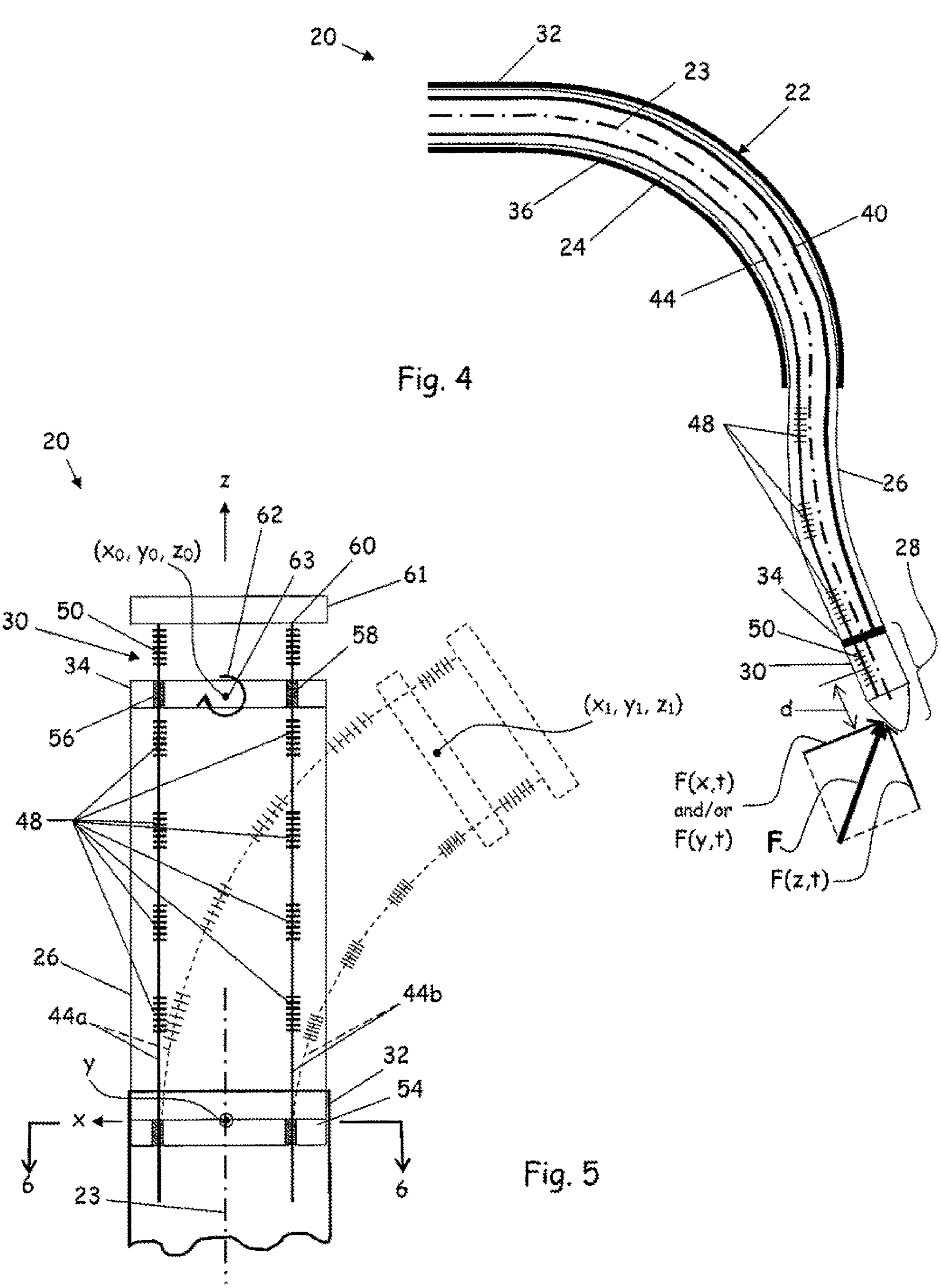
FIG. 4 is a sectional view of the manipulator arm of FIG. 3.
FIG. 5 is a partial and enlarged schematic of a section of the manipulator arm of FIG. 3 in operation.

Referring to FIGS. 3 through 5, the manipulator arm 20 is depicted as having a plurality of push-pull cables 40 that run the length of the elongate flexible body 22 in an embodiment of the invention. In this embodiment, there are four push-pull cables 40 in uniform rotational displacement 42 about the longitudinal axis 23 and operatively coupled with the yoke portion 34. The FIG. 3 embodiment also includes a trio of fiber optics 44*a*, 44*b* and 44*c* (aka optical fiber cores) also in uniform rotational displacement 46.

In one embodiment, each of the fiber optics 44*a*, 44*b*, 44*c* includes a plurality of flexing portion fiber Bragg gratings 48 for determining the shape of the flexing portion 26, and/or the location of the distal portion 30. The flexing portion fiber Bragg gratings 48 may be positioned on the respective fiber optic 44*a*, 44*b* or 44*c* such that the fiber Bragg gratings 48 are disposed within the flexing portion 26.

Figures 8, 8A:
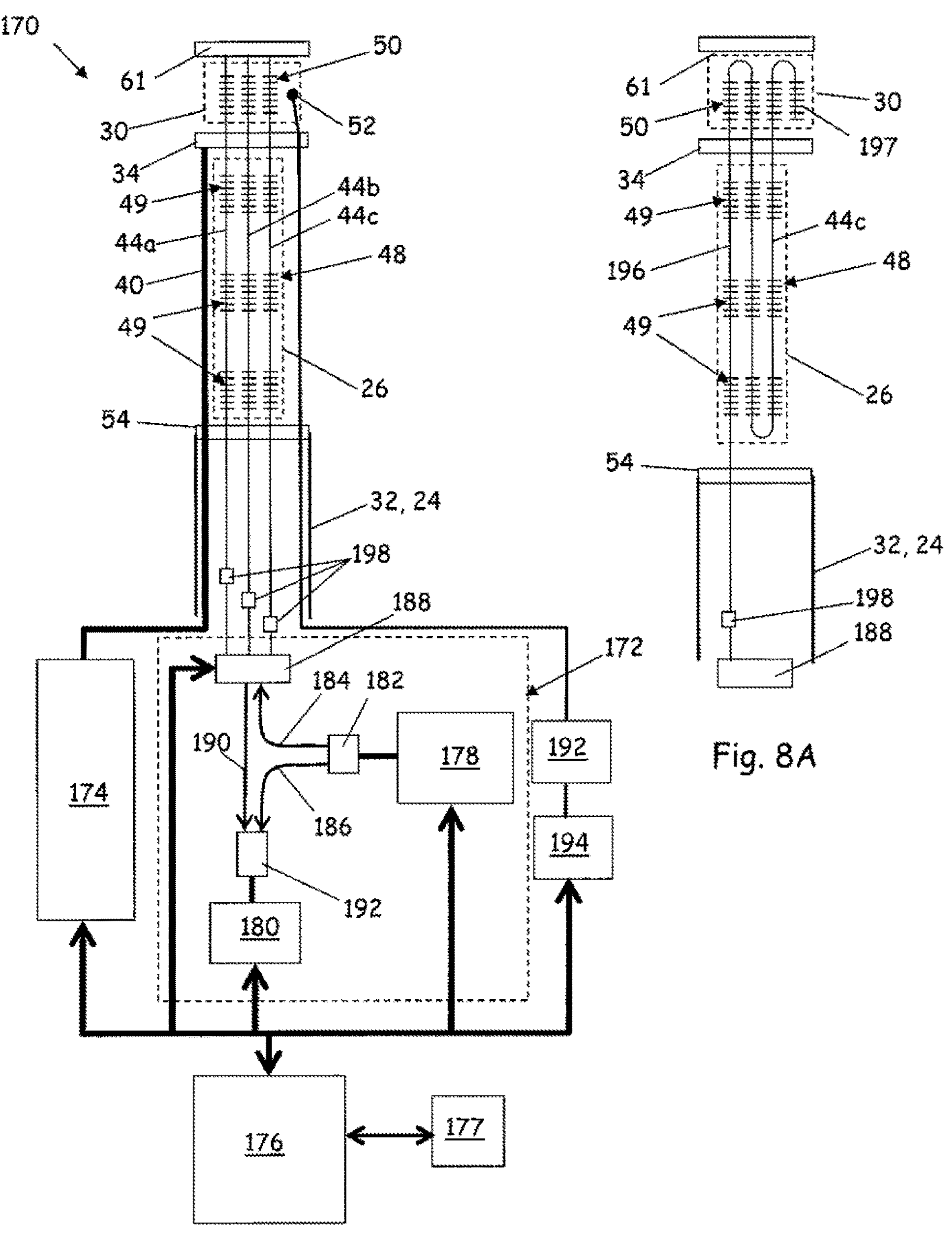
FIG. 8 is a schematic of a force manipulator system in an embodiment of the invention.
FIG. 8A is a partial schematic of a force manipulator system in an embodiment of the invention.

The fiber optics 44*a*, 44*b*, 44*c* may each have the same axial spacing between the flexing portion fiber Bragg gratings 48. A typical and non-limiting axial spacing is on the order of 1- to 2-cm. The fiber optics 44*a*, 44*b* and 44*c* may also be aligned so that the flexing portion fiber Bragg gratings 48 are grouped in "sensor triplets" 49 (i.e. three sensors located at substantially the same axial location along the z-axis) at various axial locations along the z-axis of the flexing portion 26. That is, for every flexing portion fiber Bragg grating 48 on fiber optic 44*a*, there are also corresponding flexing portion fiber Bragg gratings 48 on fiber optics 44*b* and 44*c* centered at substantially the same axial location along the flexing portion 26. The sensor triplets 49 are best depicted in FIG. 8.

At least one of the fiber optics 44*a*, 44*b* and/or 44*c* also extends through or past the yoke portion 34 and includes a distal fiber Bragg grating 50, disposed in and operatively coupled to the distal portion 30. The distal fiber Bragg grating(s) 50 may be utilized to determine a force component or components exerted on the distal portion 30 (e.g. such as described in the discussion attendant FIG. 7).

It is understood that the force component "exerted on" the distal portion 30 may be the result of an object moving into contact with a substantially stationary distal portion 30, or the result of reaction forces caused by moving the distal portion 30 into contact with a substantially stationary member, or a combination thereof.

One or more temperature sensors 52 (FIG. 3) may also extend through the elongate flexible body 22 and be operatively coupled proximate the distal fiber Bragg gratings 50.

In FIG. 5, two of the fiber optics 44*a* and 44*b* of the manipulator arm 20 are schematically depicted in an embodiment of the invention and to illustrate the operation of the invention generally. The fiber optics 44*a* and 44*b* are each depicted as having the flexing portion and the distal fiber Bragg gratings 48, 50. In this embodiment, the fiber optics 44*a* and 44*b* are connected to a base 54 operatively coupled to the rigid member 32 at the interface between the proximal portion 24 and the flexing portion 26. The center of this interface may also be utilized to define the origin of an x-y-z coordinate system, as depicted in FIG. 5.

The fiber optics 44*a* and 44*b* may extend through the yoke portion 34 and may also be securely connected to the yoke portion 34 at anchor locations 56. Each of the anchor locations 56 may be affected by a potting- or adhesive-filled orifice 58 that bonds the respective fiber optic 44*a* and 44*b* to the yoke 34. Each of the fiber optics 44*a* and 44*b* includes a distal extremity 60 that may be operatively coupled to a force transfer member 61. The elongate flexible body 22, or portions thereof, may include or be contained within a braided sleeve 36.

In operation, the push-pull cables 40 may cooperate with each other to impart a torsion or moment 64 about the yoke portion 34 that causes the flexing portion 26 to flex and the yoke portion 34 to move from a default or "at rest" position ($x_0$, $y_0$, $z_o$) to an activated position ($x_1$, $y_1$, $z_1$). In the FIG. 5 depiction, the moment 62 is about a moment axis 63 that is perpendicular to the plane containing the two fiber optics 44*a* and 44*b*, which causes the yoke portion 34 to exert a tension load on fiber optic 44*a* and a compression load on fiber optic 44*b*. The tension/compression loads cause a change in the spacing of the respective flexing portion fiber Bragg gratings 48, which in turn shifts the wavelength of the light waves reflected by the fiber Bragg gratings 48.

Inference of position may be based on the differential strain between individual flexing portion fiber Bragg gratings 48 of a given sensor triplet 49. (See Eqn. (6) and attendant discussion below.) It was previously thought that the dependence on differential strains made the shape determination insensitive to temperature changes because the thermal expansion/contraction of one strain sensor would be matched by the thermal expansion/contraction of the other strain sensors of the sensor triplet 49. This is true only where the temperature changes of flexing portion 26 are tangentially uniform at the location of the sensor triplet 49. In some applications, such as catheter systems that generate high thermal energy (e.g. ablation catheters), thermal gradients in the surroundings may cause one portion or side of the flexing portion 26 to be at a different temperature than another portion or side, thereby introducing a temperature gradient between individual flexing portion fiber Bragg gratings 48 of the same sensor triplet 49.

Figures 7, 7A, 7B, 7C:
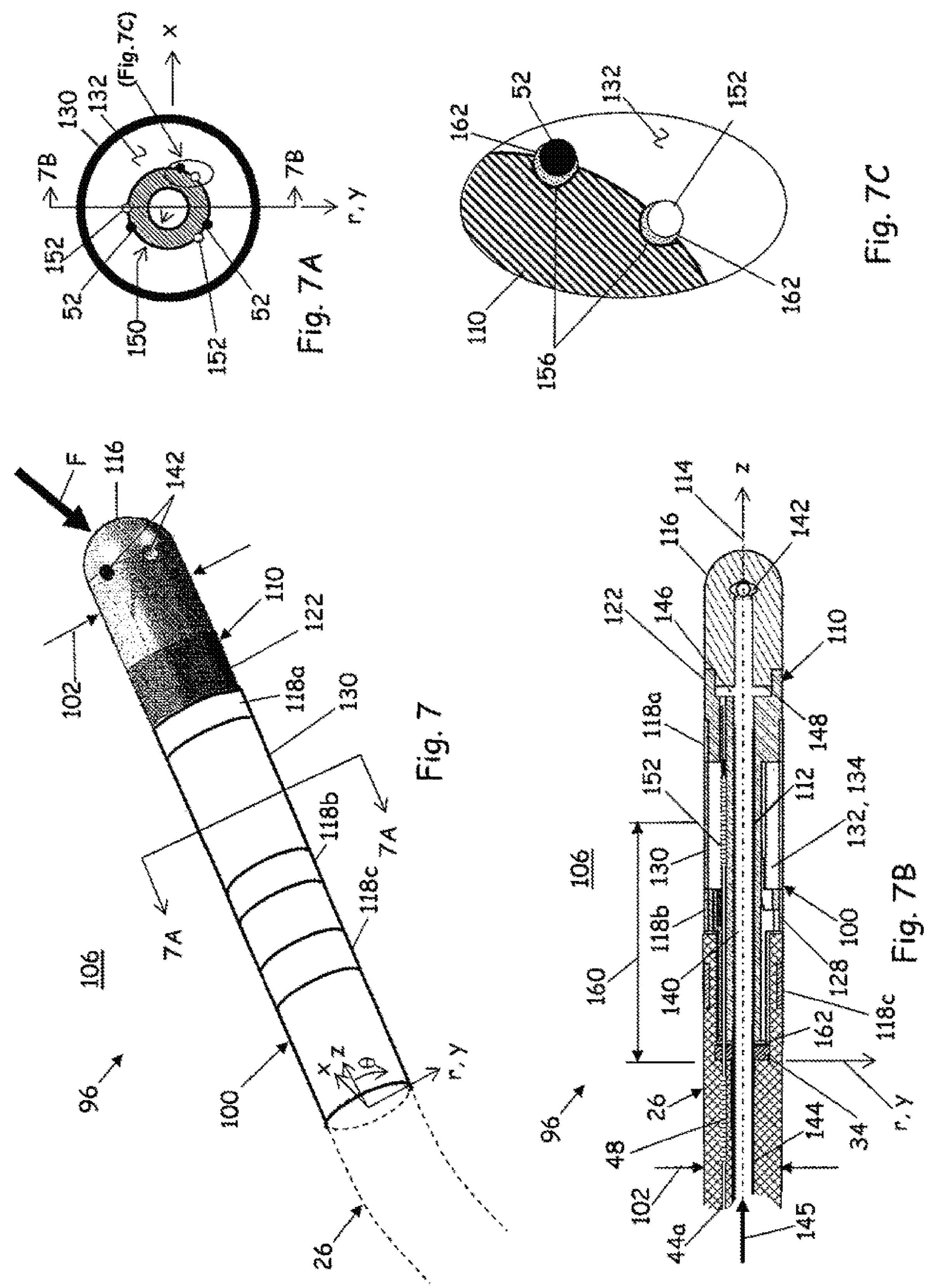
FIG. 7 is a perspective view of an end effector having a force sensor assembly and an ablation head in an embodiment of the invention.
FIGS. 7A and 7B are sectional views of the force sensing assembly of FIG. 7.
FIG. 7C is an enlarged partial view of the sectional view of FIG. 7A.

To remedy against tangential thermal gradients, the flexing portion fiber Bragg gratings 48 may be coupled closely to the irrigation source passage 144, as depicted in FIG. 7B. This way, the temperature of the flexing portion fiber Bragg gratings 48 may be dominated by the flow of the irrigation fluid 145 and also isolated from the operating environment 106 by a greater thickness of the flexible material that comprises the flexing portion 26.

The fiber optics 44*a* and 44*b* may be coupled with the yoke portion 34, and the portion of the fiber optics 44*a* and 44*b* in the distal portion 30 (i.e. between the potting-filled orifices 58 and the force transfer member 61) are isolated from compression and tension loads experienced in the flexing portion 26. By this arrangement, the distal fiber Bragg gratings 50 included in the distal portion 30 theoretically do not experience a strain due to the flexing of the flexing portion 26. In practice, the forces exerted on the yoke portion 34 may cause some flexure of the end effector 28 relative to a neutral orientation, which may translate to a detectable strain on the distal fiber Bragg gratings 50. These effects are generally repeatable and thus can be calibrated and compensated as a function of the position (e.g. x-y-z location) relative to the distal portion 30.

The temperature sensor 52 may be positioned proximate the distal fiber Bragg gratings 50 to estimate the temperature of the distal fiber Bragg gratings 50.

The number of components of the force vector that can be resolved is limited by the number of distal fiber Bragg gratings 50. That is, a single distal fiber Bragg grating 50 will resolve only a strain that is parallel to its length, and at best can only infer the local axial force component. A pair of distal fiber Bragg gratings 50 may define an axial and a tangential force component, assuming a neutral axis between the two distal fiber Bragg gratings 50. And a trio of distal fiber Bragg gratings 50 will resolve an axial component (i.e. a z-axis component) and orthogonal tangential force components (i.e. x- and y-axis components), which further enables determination of the three-dimensional orientation of the force vector.

The braided sleeve 36 may provide a degree of stiffness to the flexing portion 26 that is desirable for certain applications. For embodiments where the elongate flexible body 22 moves relative to the rigid member 32, the braided sleeve 36 may also provide abrasion resistance.

The tension/compression of the flexing portion fiber Bragg gratings 48 for a given bend may vary depending on the orientation of the respective fiber optic 44*a*, 44*b* or 44*c* relative to the plane of bending. For example, for the bending in the plane that contains both fiber optic 44*a* and 44*b* (such as depicted in FIG. 5), fiber optic 44*c* is located equidistant between the fiber optics 44*a* and 44*b* and may conform to a neutral axis or plane such that the flexing portion fiber Bragg gratings positioned thereon experience little or negligible strain.

The use of three or more push-pull cables enables an operator to control the position of the yoke portion 34 in three dimensions. The invention may be configured with just two push-pull cables, enabling control of a lateral movement or with a pull-wire that cooperates with a plane and a leaf spring to return the catheter the straight position (not depicted). The number and arrangement of push-pull cables 40 may be configured to provide bending in a plurality of planes. Accordingly, the flexing portion fiber Bragg gratings 48 on any one of the fiber optics 44 may experience varying degrees of tension, compression. In some configurations, some of the flexing portion fiber Bragg gratings 48 on a given fiber optic 44 may experience a tension while others on the same fiber optic 44 may experience a compression.

Referring to FIGS. 6A through 6D, the base 54 may also be configured to slide along the rigid member 32 in other embodiments of the invention. For example, where a rigid tube is utilized as the rigid member 32, the base 54 may be dimensioned for sliding engagement with the interior of the tube. The tube may have a non-circular cross-section, such as the oval shape depicted in FIG. 6A, or be configured to cooperate with a non-circular center guide 64, such as the square cross-sectional rod depicted in FIG. 6B. The cross-section of the base 54 may cooperate with a track structure 66, such as a tongue and groove structure formed with the rigid member 32 (FIG. 6C) or a plurality of guide rods 68 located within the proximal portion 24. While the rigid members depicted in FIGS. 6A through 6D comprise hollow tubular structures, it is understood that other support structures such as rods, cages or brackets may be utilized for the rigid member 32.

Functionally, the various cross-sections depicted in FIGS. 6A through 6D limit the rotation or twisting of the base 54 relative to the rigid member 32 while enabling movement of the base 54 along the longitudinal axis 23.

Referring to FIGS. 7 and 7A through 7C, an end effector 96 including a strain sensing assembly 100 is depicted in an embodiment of the invention. The end effector 96 may be utilized as the end effector 28 of FIG. 4. The temperature compensated strain sensing assembly 100 may have an overall diameter 102 and is depicted as being immersed in an operating environment 106. The temperature compensated strain sensing assembly 100 includes a deformable body 110 having an outer surface 112 and defining a central axis 114. In the depicted embodiment, the temperature compensated strain sensing assembly 100 comprises an ablation head 116 operatively coupled to the deformable body 110, and external sleeve electrodes 118*a*, 118*b* and 118*c*. An external force vector F is depicted as being applied to the ablation head 116. Dual coordinate systems (i.e. Cartesian x-y-z and cylindrical r-θ-z) are depicted at the base of the deformable body 110.

The deformable body 110 may include a collar portion 122, a neck portion 124 having a neck radius 126, a radial standoff structure 128, and an outer sleeve 130 that surrounds the neck portion 124. The outer sleeve 130 may bridge between the radial standoff structure 128 and the collar portion 122 and cooperate with the neck portion 124 to define an annular gap 132. The annular gap 132 may include a thermal insulator 134.

An irrigation passage 140 may be defined as passing through the deformable body 110 and the ablation head 116, and may terminate at irrigation outlets 142 formed in the ablation head 116. An irrigation source passage 144 may be operatively coupled with the irrigation passage 140 for sourcing the irrigation passage 140 with irrigation fluid 145. An axial gap 146 may be defined between the deformable body 110 and a base surface 148 of the ablation head 116.

In one embodiment, a representative wall thickness 150 is approximately 200- to 300-micrometers; however, this wall thickness may not be representative or limiting for all embodiments.

A plurality of optical fiber strain sensors 152 may be operatively coupled to the deformable body 110. The one more temperature sensors 52 may also be operatively coupled to the deformable body 110. In one embodiment (depicted), the number of temperature sensors 52 is equal to the number of distal fiber Bragg gratings 50, one temperature sensor 52 for a corresponding distal fiber Bragg grating 50, with the sensitive portion of temperature sensor 52 being mounted in close proximity to the corresponding distal fiber Bragg grating 50. Channels 156 may be defined on the outer surface 112 of the deformable body 110 and the sensors 152, 52 coupled thereto. The sensitive portions of the optical fiber strain sensors 152 and temperature sensor(s) 52 may be substantially centered at the same axial location 160 relative to a proximal end 162 of the deformable body 110.

Generally, the deformable body 110 may comprise a polymeric material such as liquid crystal polymer (LCP) or polyetheretherketone (PEEK). Generally, the deformable body 110 is stiffer than the flexing portion 26 of the catheter so that deformable body 110 does not flex under its own weight and cause the optical fiber strain sensors 152 to undergo an orientation, non-force related strain. The channels 156 may aid in the precise location of the sensitive portions of the sensors 50, 52. Each optical fiber strain sensor 152 may comprise a fiber Bragg grating sensor (e.g distal fiber Bragg grating 50) or a Fabry-Perot sensor.

Operative coupling of the optical fiber strain sensor 152 and/or the temperature sensor(s) 52 may be accomplished in one embodiment using a glue 162. The glue 162 may be placed in the channels 156 or on the optical fiber strain sensors 152 and the strain sensors 152 placed in the channels 156. Excess glue may be removed after placement. Some glues may enable placement of the optical fiber strain sensors 152 in the channels 156 followed by a coating or dabbing of glue on the optical fiber strain sensors 152 to secure it to the channels 156.

Another bonding technique may involve the use of a solvent designed to cause the material of the deformable body 110 to melt or flow while not affecting the material of the strain sensors 152. The solvent may be applied to an area or zone of the deformable body 110 that encompasses at least a portion of the channels 156 where the strain sensors 152 are to be mounted, and the optical fiber strain sensors 152 placed therein. Alternatively, the optical fiber strain sensors 152 may be temporarily held in place in the channels 156 of the deformable body 110 and the solvent applied as a coating over both. The flowing of the material in and around the channels 156 can cause a bond between the deformable body 110 and the optical fiber strain sensors 152. The solvent may be removed by a process such as washing or evaporation to arrest the melting process.

While the mounting and bonding techniques above are directed to an embodiment that includes channels 156, it is recognized that the same procedures may be utilized in the absence of channels 156.

Dimensionally, representative and non-limiting ranges for the various parameters include the overall diameter 102 of approximately 2.3-mm, the irrigation passage 140 of approximately 0.4- to 0.8-mm diameter, and the representative wall thickness 150 on the order of 200- to 300-micrometers.

Functionally, the reduced neck radius 126 of the neck portion 124 and/or the decreased diameter of the irrigation passage 140 relative to certain existing configurations provides several advantages. For a given flow rate of irrigation fluid 145, the smaller diameter irrigation passage 140 increases the Reynolds number of the fluid flow, which can increase the convection heat transfer coefficient between the irrigation fluid 145 and the boundary of the irrigation passage 140, thereby enhancing the overall heat transfer between the irrigation fluid 145 and the optical fiber strain sensors 152. The reduced radius 126 may also provide a reduced cross-section of material, thereby reducing the thermal conductance through the neck portion 124 in the axial direction Z and the thermal coupling between the ablation head 116 and the optical fiber strain sensors 152. The wall thickness 150 of the neck portion 124 can also be tailored for a desired sensitivity (displacement) of the temperature compensated strain sensing assembly 100 in response to the force vector F. The reduced neck radius 126 of the neck portion 124 may also provide an increased thickness of the annular gap 132 relative to existing designs, thereby enhancing the thermal isolation between the operating environment 106 and the optical fiber strain sensors 152.

The channels 156, when present, may further decrease the thermal conduction path between the irrigation fluid 145 and the optical fiber strain sensors 152.

The axial gap 146, being flooded with irrigation fluid 145, may actively cool the base surface 148 of the ablation head 116 and mitigate against axial conduction of heat between the base surface 148 and the deformable body 110.

By these various thermal management aspects, various embodiments of the invention may cause the optical fiber strain sensors 152 to be dominated by the temperature of the irrigation fluid 145, with the influence of the ablation head 116 and the surroundings being secondary. An advantage of having the irrigation fluid 145 dominate the thermal state of the optical fiber strain sensors 152 is that the temperature of the irrigation fluid 145, as well as the convective coupling between the irrigation fluid 145 and the irrigation passage 140, tends to be more stable than the temperature of the ablation head 116 and the temperature and convective coupling between the operating environment 106 and the outer sleeve 130 during operation.

In operation, the temperature sensor(s) 52 may be utilized to compensate for the thermal expansion/contraction of the optical fiber strain sensors 152 relative to the calibration or nulling state. For configurations where the irrigation fluid 145 dominates the temperature of the neck portion 124, the temperature profile of the neck portion 124 may be substantially uniform or at least be substantially linear with respect to the axial coordinate Z, with no substantial variation tangentially in the temperature of the deformable body 110 at a given axial location (e.g. 160). In such conditions, a single temperature sensor 52 may be sufficient to accomplish the temperature compensation, particularly if the optical fiber strain sensors 152 and the temperature sensor 52 are positioned so the sensitive portions are centered about the same axial location 160.

Referring to FIG. 8, a force sensing manipulator system 170 comprising a detector 172 such as an optical time-domain reflectometer (OTDR) and a steering mechanism 174 is schematically depicted in an embodiment of the invention. The force sensing manipulator system 170 may also be controlled and monitored by a controller or microprocessor 176. A storage device 177 may be accessed by the microprocessor 176. The storage device may comprise a programmable read-only memory (PROM) for providing program instructions and various constants and variables used in executing the force sensing operation. The storage device 177 may also include random access memory (RAM) and/or a writable medium such as a computer disk for storage of values computed by the microprocessor 176.

The OTDR in this embodiment includes an electromagnetic source 178 and a receiver 180, both operatively coupled to a plurality of fiber optics 44. A splitter 182 may be operatively coupled with the electromagnetic source 178 that divides the electromagnetic radiation supplied by the electromagnetic source 178 into a transmitted component 184 and a reference component 186. The transmitted component may be routed through a multiplexer 188 for interrogation of an individual fiber optic (e.g. 44*a*, 44*b*, 44*c*) and the fiber Bragg gratings 48, 50 disposed thereon. A plurality of reflected components 190 may be returned from the fiber optics 44 and coupled with the reference component 186 for transmission into the receiver 180.

The temperature sensor 52 may be operatively coupled to the distal portion 30 of the manipulator arm 20 to infer the temperature of the distal fiber Bragg gratings 50. A signal conditioner 192 and digitizer 194 may be operatively coupled to the temperature sensor 52 to produce a digitized signal that may be monitored by the microprocessor 176.

Referring to FIG. 8A, an alternative arrangement is depicted for the fiber Bragg gratings 48, 50 and for sensing the temperature of the distal fiber Bragg gratings 50. In this embodiment, the flexing portion fiber Bragg gratings 48 and the distal fiber Bragg gratings 50 are all disposed on a single fiber optic 196. The single fiber optic 196 may be routed multiple times along the length of the flexing portion 26 and the distal portion, and arranged so that the flexing portion fiber Bragg gratings 48 are grouped in sensor triplets 49 and so that at least one distal fiber Bragg grating 50 is disposed in the distal portion 30.

In addition, a temperature sensing fiber Bragg grating 197 may be included on one the single fiber optic 196 and situated in the distal portion 30 proximate the distal fiber Bragg gratings 50. The temperature sensing fiber Bragg grating 197 may be mechanically isolated from the distal portion 30 so as to be free of any strain caused by forces imparted on the distal portion 30. In this way, the only dimensional and refractive index changes incurred by the temperature sensing fiber Bragg grating 197 may be due solely to temperature changes relative to a reference temperature. The temperature sensing fiber Bragg grating 197 may be interrogated with the other fiber Bragg gratings 48, 50, thus negating the need for separate routing of the temperature sensor 52 as well as the supporting instrumentation of the signal conditioner 192 and digitizer 194. The technique of using temperature sensing fiber Bragg gratings is further detailed in U.S. Patent Application Publication 2007/0060847, assigned to the assignee of the instant application, the disclosure of which is incorporated by reference except for express definitions contained therein.

Returning to FIG. 8, each of the fiber Bragg gratings 48, 50 (and 197 when applicable) of each of the fiber optics 44 (or alternatively of the single fiber optic 196) may be configured to reflect a distinct central wavelength when the fiber optic 44 or 196 is in an unstrained state. The distinct central wavelengths enable each of the fiber Bragg gratings 48, 50 on the fiber optic 44 or 196 to be identified in a process referred to as wavelength division multiplexing (WDM). The WDM technique, or techniques akin thereto, are described in numerous publications, such as U.S. Pat. No. 5,798,521 to Froggatt and U.S. Pat. No. 6,256,090 to Chen et al. and U.S. Patent Application Publication No. 2007/0065077 to Childers et al., the disclosures of which are hereby incorporated by reference other than any claims or express definitions of terms specifically defined therein. In the WDM configuration, the electromagnetic source 178 is configured to sweep a range of wavelengths, with each of the fiber Bragg gratings 48, 50 tuned to reflect light waves at a unique central wavelength within the swept wavelength range. The electromagnetic source 178 may comprise a solid state laser tunable over a range of wavelengths. An example electromagnetic source 178 is the Model SM130 tunable laser by Micron Optics, which may be configured for a tunable range 1519-nm to 1590-nm.

In another embodiment, the detector 172 may comprise an optical frequency-domain reflectometer (OFDR). The OFDR technique has been commercialized for numerous monitoring applications. Optical frequency-domain reflectometry enables sensors with the same nominal reflected wavelength to be read with very high spatial resolution for spectral analysis. With the OFDR technique, the fiber Bragg gratings 48, 50 may be interrogated with a swept wavelength source. Each of the fiber Bragg gratings 48, 50 of a given fiber optic 44 may be spaced a unique distance from a reflector 198 operatively coupled with the fiber optic 44 or 196 located in the proximal portion 24. In this way, each of the fiber Bragg gratings 48, 50 combines with the respective reflector 198 to form an interferometer with a unique optical-path difference. When interrogated with an electromagnetic source, the interferometers modulate the reflected components 190 of each grating with a unique frequency that is directly dependent on the path difference. A summary of the OFDR method is presented in Appendices A and B, copies of which are attached hereto and incorporated by reference except for express definitions therein. Note that only one reflector 198 is required for the single fiber optic 196 configuration of FIG. 8A.

Figure 9:
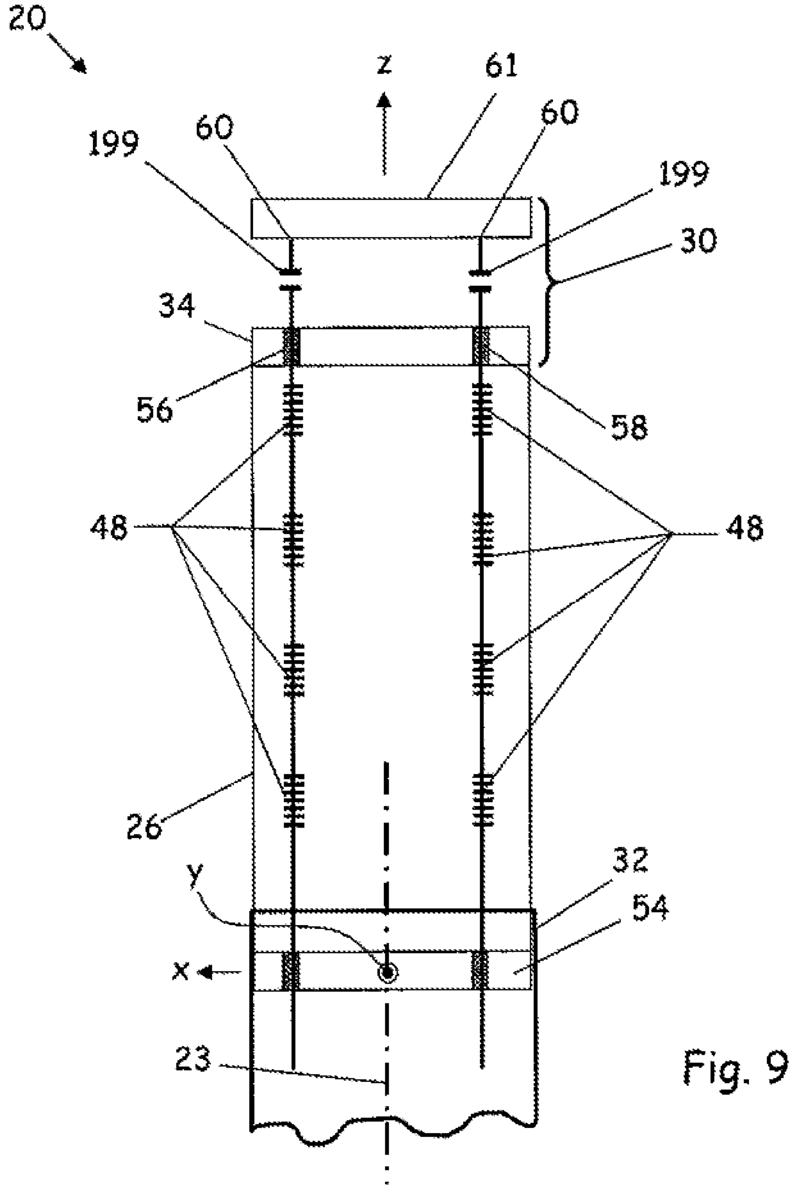
FIG. 9 is a partial and enlarged schematic of a manipulator arm in an embodiment of the invention.

Referring to FIG. 9, a manipulator arm 20 is depicted using a plurality of Fabry-Perot resonators 199 to detect the force applied to the force transfer member 61. The Fabry-Perot resonators may comprise commercially available fiber optic strain sensors, such as disclosed in U.S. Pat. Nos. 5,202,939 and 5,392,117 to Belleville, et al., disclosures of which are hereby incorporated by reference other than any express definitions of terms specifically defined therein. Other Fabry-Perot resonators may also be implemented, such as disclosed and depicted in U.S. patent application Ser. No. 11/753,429, a copy of which is attached hereto as Appendix C and which incorporated by reference except for express definitions therein. U.S. patent application Ser. No. 11/753,429 is also assigned to the assignee of the instant application.

The Fabry-Perot resonators 199 may be selected to return a modulated signal from a selected portion of the spectrum of the electromagnetic source 178 that is functionally outside the operating ranges of the various flexing portion fiber Bragg gratings 48, so as not to be attenuated by the flexing portion fiber Bragg gratings 48. When the electromagnetic source 178 operates at this selected portion of the spectrum, the force sensing manipulator system 170 analyzes the returned modulated signal accordingly.

Functionally, the Fabry-Perot resonators 199 may be configured to provide certain advantages, including substantial insensitivity to bulk temperature changes and thermal gradients. The use of Fabry-Perot resonators may be more suitable with the OFDR technique.

A method for determining the position of the yoke portion 34 or the distal portion 30 or any arbitrary point on the elongate flexible body 22 is disclosed by Zhang, et al., "On SDM/WDM FBG Sensor Net for Shape Detection of Endoscope," Proceedings of the IEEE, International Conference on Mechatronics and Automation, July 2005, included herein as Appendix D, a copy of which is attached hereto and which incorporated by reference except for express definitions therein. Other methods may also be utilized to infer position from the signals reflected from the flexing portion fiber Bragg gratings 48, such as described by U.S. Published Patent Application 2007/0065077 to Childers et al., previously incorporated by reference herein.

Referring to FIGS. 10 through 13, a method for determining shape and location from the strains experienced by the flexing portion fiber Bragg gratings 48 is described. The flexing portion 26 may be divided into segments 210, each segment 210 being centered about one of the sensor triplets 49 disposed in the flexing portion 26 and including three core segments 212*a*, 212*b* and 212*c*, one for each member of the sensor triplet 49. The sensor triplets 49 may be evenly spaced segments along longitudinal axis 23 of the flexing portion fiber Bragg gratings 48. Strain values for each flexing portion fiber Bragg grating 48 contained in the segment 210 may be used to compute a direction β of the bend angle θ and a bend radius r for each of the segments 210. Starting, for example, at the base 54 at the interface between the proximal portion 24 and the flexing portion 26 (FIG. 5), the direction β and radius r data may be built up or accumulated to compute the location in the x, y, z coordinate system of each successive segment 210 along the flexing portion 26 and to define a new local coordinate system x', y', z', herein referred to as the sensor frame coordinate system, for each successive sensor triplet 49. In one embodiment, the sensor frame coordinate system has its origin at the center of the perimeter of the object for any given sensor triplet 49. The circular arcs between each sensor triplet 49 on the flexing portion 26 may be interpolated. The geometry of the flexing portion 26 can thus be determined by repeating the accumulation, sensor frame coordinate system definition and interpolation process for each segment 210 and sensor triplet 49 along the length of the flexing portion 26. The z' axis may point in the direction normal to the cross-section of the segment 210 and the y' axis may be aligned one of the fiber optics 44 (see FIGS. 10A and 10B).

For a given sensor triplet 49, a trio of strain values ε1, ε2, ε3 may be detected, one from each member of the sensor triplet 49. From the strain values ε1, ε2, ε3, one can calculate the direction β of the bend with respect to the x' axis as well as a bend radius r about an axis of rotation 214, defined as the distance from the center of curvature to the center of the core perimeter (see FIG. 13). Knowing the bend radius r and direction β for a particular segment 210 of the flexing portion 26, computation of the coordinates of the end of the segment in the (x', y', z') coordinate system may be performed.

The beginning of the fiber segment 210 may be taken to be the origin of the (x', y', z') system. When there is no curvature, each core segment 44*a* has a length s. When a curvature is introduced, each core is generally a different distance r1, r2 and r3 from the center of curvature, as shown in FIG. 12B. Because all of the core segments subtend the same curvature angle θ, each segment will generally have a unique length. The change in length due to bending the fiber is denoted as ds1, ds2 and ds3 (FIG. 12B).

The equations relating the change in length and radius of curvature of each fiber to the other fibers are derived as:

$$\theta = \frac{s + ds1}{r1} = \frac{s + ds2}{r2} = \frac{s + ds3}{r3} \qquad \text{Eqn. (1)}$$

Because elastic strain (denoted by ε) is defined as the ratio of the change in length of the fiber, ds to its unstretched length s (i.e. ε=ds/s) the first part of Eqn. (1) may be written in terms of the measured strains:

$$\theta = \frac{s + ds1}{r1} = s\left(\frac{1 + ds/s1}{r1}\right) = s\left(\frac{1 + \varepsilon 1}{r1}\right) \qquad \text{Eqn. (2)}$$

Accordingly, with respect to the other terms of Eqn. (1) the following expression results:

$$\frac{1 + \varepsilon 1}{r1} = \frac{1 + \varepsilon 2}{r2} = \frac{1 + \varepsilon 3}{r3} \qquad \text{Eqn. (3)}$$

To solve Eqn. (3) for r and β, r1, r2 and r3 are written in terms of r and β. This can be done by analyzing the geometry of the fiber cross-section (FIG. 11) and results in the following expressions for the radii of curvature for each of the fibers:

$$r1 = r + a\cdot\sin(\beta)$$

$$r2 = r + a\cdot\sin(\beta + \Phi 12)$$

$$r3 = r + a\cdot\sin(\beta - 13) \qquad \text{Eqn. (4)}$$

where a is the radial distance of the individual fiber Bragg gratings of a given sensor triplet 49 from the z-axis (FIG. 11) Substituting Eqns. (4) to make substitutions into Eqns. (3), the following three equations are derived for r and β:

$$(1+\varepsilon 1)(r + a\cdot\sin(\beta + \Phi 12)) = (1+\varepsilon 2)(r + a\cdot\sin(\beta))$$

$$(1+\varepsilon 1)(r + a\cdot\sin(\beta + \Phi 13)) = (1+\varepsilon 3)(r + a\cdot\sin(\beta))$$

$$(1+\varepsilon 2)(r + a\cdot\sin(\beta + \Phi 13)) = (1+\varepsilon 3)(r + a\cdot\sin(\beta + \Phi 12)) \qquad \text{Eqn. (5)}$$

Equation (5) may be solved for β using the trigonometric identity $$\tan\beta = \frac{\varepsilon 13\cdot\sin\phi 12 + \varepsilon 12\cdot\sin\phi 13}{\varepsilon 23 - \varepsilon 13\cdot\sin\phi 12 + \varepsilon 12\cdot\sin\phi 13} \qquad \text{Eqn. (6)}$$

where ε12=ε2−ε1, ε13=ε3−ε1 and ε23=ε3−ε2.

Note that each term in the Eqn. (6) numerator and denominator is proportional to a strain difference. That is, the bend direction β is dependent only on the differential strains, not the absolute strain values.

The bend radius r can be computed in three different ways. Each of these formulae give the same solution for r, but in practice it is advantageous to implement at least two in case one of the differential strains ε12, ε13 or ε23 is zero.

$$r = \frac{a}{\varepsilon 12}(\sigma 1 \cdot \sin(\beta + \phi 12) - \sigma 2 \cdot \sin(\beta)) \quad \text{Eqn. (7)}$$

$$r = \frac{a}{\varepsilon 13}(\sigma 1 \cdot \sin(\beta - \phi 13) - \sigma 3 \cdot \sin(\beta))$$

$$r = \frac{a}{\varepsilon 23}(\sigma 2 \cdot \sin(\beta - \phi 13) - \sigma 3 \cdot \sin(\beta + \phi 12))$$

where σ1=(1+ε1), σ2=(1+ε2) and σ3=(1+ε3).

From Eqn. (6), the domain of the bend direction β is −π/2<β<π/2. The extra π radians appear in the calculation of the bend radius r. That is, if r is negative, simply negate r and add π to β. After this operation, r>0 and 0≤β<2π. Also, where ε1=ε2=ε3, a special case arises where the bend direction β may be considered arbitrary because the bend radius r is infinite (zero curvature).

Resolution of a force vector (magnitude and direction) that is incident on the distal portion 30 may be inferred from strain measurements of the distal fiber Bragg gratings 50. In one embodiment, one of the distal fiber Bragg gratings 50 may reflect a reference wavelength λr when the distal fiber Bragg grating 50 is at a reference temperature Tr at a reference time r when a reference or null measurement is performed. During operation, the distal fiber Bragg grating 50 may reflect a wavelength λt at time t relative to the reference time r. The wavelength λt from the distal fiber Bragg grating 50 may differ from the respective reference wavelength λr due to a change in the length ΔL of the distal fiber Bragg grating 50 relative to its length L at time r.

The change in the length ΔL may be caused by a strain on the distal fiber Bragg grating 50, a temperature change that induces a thermal expansion of the distal fiber Bragg grating 50, or a combination thereof Δn apparent strain ΔL/L may therefore be expressed as $$\Delta L/L = C\varepsilon \cdot (\lambda t - \lambda r) = \varepsilon + \alpha \Delta T \quad \text{Eqn. (8)}$$

$$\text{where } \Delta T = Tt - Tr \quad \text{Eqn. (9)}$$

and Cε is the coefficient of linearity between the FBG reflected wavelength and apparent strain, ε is the elastic strain imposed on the distal fiber Bragg grating 50, α is an equivalent coefficient of thermal expansion for the distal fiber Bragg grating 50, and ΔT is the difference between the temperature Tt of the distal fiber Bragg grating 50 at time t and the reference temperature Tr. The apparent strain ΔL/L is so named because, without knowledge of the temperature and thermal behavior of the optical fiber sensor, the ratio ΔL/L would appear to be the result of an elastic strain.

Generally, it is desirable to mathematically isolate the elastic strain ε because it is primarily due to axial forces imposed on the distal fiber Bragg grating 50. Isolating the elastic strain gives $$\varepsilon = \Delta L/L - \alpha \cdot \Delta T = C\varepsilon \cdot (\lambda t - \lambda r) - \alpha \cdot \Delta T \quad \text{Eqn. (10)}$$

For a plurality of distal fiber Bragg gratings 50, Eqn. (10) may be expressed by $$\varepsilon_i = (\Delta L/L)_i - \alpha_i \cdot \Delta T_i = C\varepsilon \cdot )\lambda t - \lambda r)_i - \alpha_i \cdot \Delta T_i \quad \text{Eqn. (11)}$$

where the subscript i denotes one of a plurality of distal fiber Bragg grating 50.

But for the effects of temperature change on the optical fiber sensors, the apparent strain $\Delta L/L_i$ is equal to the elastic strains $\varepsilon_i$. Accordingly, the product $\alpha_i \cdot \Delta T_i$ may be considered a thermal bias component of the respective apparent strain $\Delta L/L_i$.

The equivalent coefficient of thermal expansion α is a parameter that is influenced by many factors. In some embodiments, α is influenced primarily by the coefficient of thermal expansion (CTE) of the distal portion 30. The CTE of the fiber Bragg grating 50 may also be a contributing factor, as well as the CTE of the attachment mechanism (e.g. glue 162 or potting) between the distal portion 30 and the fiber Bragg grating 50. The range of the CTEs of these components can vary substantially. For example, the CTE of the optical fiber Bragg grating 50 can be on the order of about 0.3 micrometers per Kelvin (μ/K), whereas the CTE of a distal portion 30 constructed of LCP may have a CTE from 1- to 4-μ/K. Some glues can have a CTE on the order of 60 μ/K.

Furthermore, the refractive index of the optical fiber Bragg grating 50 may be sensitive to changes in temperature. The sensitivity of the refractive index of some optical fibers is on the order of 10 picometers per Kelvin (pm/K). Depending on the configuration (e.g. geometry, CTEs of the various materials, sensitivity of the refractive index to temperature), the influence of the refractive index change may be dominant. For example, the resultant changes due to refractive index changes have been known to be an order of magnitude greater than the influence of CTE changes.

The true equivalent coefficient of thermal expansion α is generally affected by imperfections and/or non-repeatability of the assembly. For example, the equivalent coefficient of thermal expansion α of an optical fiber sensor may be substantially affected by minute differences in the amount of glue utilized to affect the bond. Accordingly, each of the fiber Bragg gratings 50 in a given strain sensing assembly is generally characterized by its own unique equivalent coefficient of thermal expansion α.

All of these thermal influences are rolled into the equivalent coefficient of thermal expansion α. Moreover, the complexity of the parameter may cause α to be non-linear. Accordingly, it is often preferable to determine the equivalent coefficient of thermal expansion α experimentally, such as by calibration, and for each optical fiber strain sensor in an assembly.

A method for determining the force exerted on the distal portion 30 from the distal fiber Bragg gratings 50 is now described. Consider a manipulator arm 20 having three fiber optic Bragg strain sensors embedded within the distal portion 30, the distal portion 30 being comprised of a polymer, for example liquid crystal polymer (LCP). The total strain may be computed using:

$$\begin{bmatrix} \Delta L/L(1,t) \\ \Delta L/L(2,t) \\ \Delta L/L(3,t) \end{bmatrix} = \begin{bmatrix} C\varepsilon & 0 & 0 & C\varepsilon T \\ 0 & C\varepsilon & 0 & C\varepsilon T \\ 0 & 0 & C\varepsilon & C\varepsilon T \end{bmatrix} \cdot \left( \begin{bmatrix} \lambda(1,t) \\ \lambda(2,t) \\ \lambda(3,t) \end{bmatrix} - \begin{bmatrix} \lambda(1,r) \\ \lambda(2,r) \\ \lambda(3,r) \end{bmatrix} \right) \quad \text{Eqn. (12)}$$

where: r≡time when reference (zero) measurement is set;

t≡time relative to reference time;

λ(i,r)≡reference wavelengths of the three fiber Bragg gratings i=1−3 at time r;

λ(i,t)≡active wavelengths of the three fiber Bragg gratings i=1−3 at time t;

ΔL/L(i,t)≡apparent strain of the three fiber Bragg gratings i=1−3 at time t;

ΔT(t)≡temperature change at time t relative to a reference temperature at time r;

Cε≡coefficient of linearity between the reflected wavelength and strain; and

CεT≡coefficient of temperature compensation of the fiber Bragg gratings.

Where the temperature sensing fiber Bragg grating 197 is implemented to determine ΔT(t), Eqn. (12) may be expressed as $$\begin{bmatrix} \Delta L/L(1,t) \\ \Delta L/L(2,t) \\ \Delta L/L(3,t) \\ \Delta T(t) \end{bmatrix} = \begin{bmatrix} C\varepsilon & 0 & 0 & C\varepsilon T \\ 0 & C\varepsilon & 0 & C\varepsilon T \\ 0 & 0 & C\varepsilon & C\varepsilon T \\ 0 & 0 & 0 & CT \end{bmatrix} \cdot \left( \begin{bmatrix} \lambda(1,t) \\ \lambda(2,t) \\ \lambda(3,t) \\ \lambda(4,t) \end{bmatrix} - \begin{bmatrix} \lambda(1,r) \\ \lambda(2,r) \\ \lambda(3,r) \\ \lambda(4,r) \end{bmatrix} \right) \quad \text{Eqn. (13)}$$

where λ(4,r) and λ(4,t) are, respectively, the reference and active wavelengths from the temperature sensing fiber Bragg grating 197.

In general, the total strain includes a component due to thermal expansion of the deformable body arising from the difference between the measured temperature of the deformable body and a predetermined reference temperature. The elastic strain, which is a function of the applied force, therefore may be calculated using:

$$\begin{bmatrix} \varepsilon(1,t) \\ \varepsilon(2,t) \\ \varepsilon(3,t) \end{bmatrix} = \begin{bmatrix} 1 & 0 & 0 & -\alpha 1 \\ 0 & 1 & 0 & -\alpha 2 \\ 0 & 0 & 1 & -\alpha 3 \end{bmatrix} \cdot \begin{bmatrix} \Delta L/L(1,t) \\ \Delta L/L(2,t) \\ \Delta L/L(3,t) \\ \Delta T(t) \end{bmatrix} \quad \text{Eqn. (14)}$$

where ε(i,t) and αi are, respectively, the elastic strain and the equivalent coefficient of thermal expansion of the three fiber Bragg gratings i=1-3 at time t.

Where temperature sensors 52 are provided for each of the trio of distal fiber Bragg gratings 50, the elastic strain may be calculated by:

$$\begin{bmatrix} \varepsilon(1,t) \\ \varepsilon(2,t) \\ \varepsilon(3,t) \end{bmatrix} = \begin{bmatrix} 1 & 0 & 0 & -\alpha 1 & 0 & 0 \\ 0 & 1 & 0 & 0 & -\alpha 2 & 0 \\ 0 & 0 & 1 & 0 & 0 & -\alpha 3 \end{bmatrix} \cdot \begin{bmatrix} \Delta L/L(1,t) \\ \Delta L/L(2,t) \\ \Delta L/L(3,t) \\ \Delta T(1,t) \\ \Delta T(2,t) \\ \Delta T(3,t) \end{bmatrix} \quad \text{Eqn. (15)}$$

or $$\begin{bmatrix} \varepsilon(1,t) \\ \varepsilon(2,t) \\ \varepsilon(3,t) \end{bmatrix} = \begin{bmatrix} C & 0 & 0 & -\alpha 1 & 0 & 0 \\ 0 & C & 0 & 0 & -\alpha 2 & 0 \\ 0 & 0 & C & 0 & 0 & -\alpha 3 \end{bmatrix} \cdot \left( \begin{bmatrix} \lambda(1,t) \\ \lambda(2,t) \\ \lambda(3,t) \\ T(1,t) \\ T(2,t) \\ T(3,t) \end{bmatrix} - \begin{bmatrix} \lambda(1,r) \\ \lambda(2,r) \\ \lambda(3,r) \\ T(1,r) \\ T(2,r) \\ T(3,r) \end{bmatrix} \right) \quad \text{Eqn. (16)}$$

where T(i,r) are the inferred reference temperature readings of the three fiber Bragg gratings i=1-3 at time r and T(i,t) are the inferred active temperature readings of the three fiber Bragg gratings i=1-3 at time t. Both T(i,r) and T(i,t) may be inferred from the plurality of temperature sensors 52.

The elastic strains are related to the internal forces experienced by the optical fiber sensors as a function of both the physical dimensions of, and the material properties of, the deformable body:

$$\begin{bmatrix} \varepsilon(1,t) \\ \varepsilon(2,t) \\ \varepsilon(3,t) \end{bmatrix} = \begin{bmatrix} 1 & y1 & -x1 \\ 1 & y2 & -x2 \\ 1 & y3 & -x3 \end{bmatrix} \cdot \begin{bmatrix} \frac{1}{E_T \cdot A} & 0 & 0 \\ 0 & \frac{1}{E_F \cdot Ix} & 0 \\ 0 & 0 & \frac{1}{E_F \cdot Iy} \end{bmatrix} \cdot \begin{bmatrix} N(z,t) \\ M(x,t) \\ M(y,t) \end{bmatrix} \quad \text{Eqn. (17)}$$

where: xi and yi≡coordinate locations of the distal fiber Bragg gratings 50 relative to a reference point (e.g. center of gravity) of the catheter cross-section;

$E_T$≡equivalent tension/compression Young modulus of the catheter;

$E_F$≡equivalent flexural Young modulus of the catheter;

Ix≡moment of inertia of the catheter cross-section about the x-axis;

Iy≡moment of inertia of the catheter cross-section about the y-axis;

N(z,t)≡normal force in the direction of the z-axis at time t;

M(x,t)≡bending moment about the x-axis at time t; and

M(y,t)≡bending moment about the y-axis at time t.

Equation (17) may be rearranged to solve for the internal forces as a function of the elastic strain:

$$\begin{bmatrix} N(z,t) \\ M(x,t) \\ M(y,t) \end{bmatrix} = \begin{bmatrix} E_T \cdot A & 0 & 0 \\ 0 & E_F \cdot Ix & 0 \\ 0 & 0 & E_F \cdot Iy \end{bmatrix} \cdot \begin{bmatrix} 1 & y1 & -x1 \\ 1 & y2 & -x2 \\ 1 & y3 & -x3 \end{bmatrix}^{-1} \cdot \begin{bmatrix} \varepsilon(1,t) \\ \varepsilon(2,t) \\ \varepsilon(2,t) \end{bmatrix} \quad \text{Eqn. (18)}$$

It remains only to relate the internal forces N(z,t), M(x,t) and M(y,t) experienced by the optical fiber sensors to the external contact or reaction forces F exerted on the distal extremity of the end effector 28. These forces are computed based on the positions of the optical fiber sensors from the exterior wall of the deformable body, assuming the deformable body is substantially incompressible:

$$\begin{bmatrix} F(x,t) \\ F(y,t) \\ F(z,t) \end{bmatrix} = \begin{bmatrix} 0 & 0 & -\frac{1}{d} \\ 0 & \frac{1}{d} & 0 \\ -1 & 0 & 0 \end{bmatrix} \cdot \begin{bmatrix} N(z,t) \\ M(x,t) \\ M(y,t) \end{bmatrix} \quad \text{Eqn. (19)}$$

where: F(x,t)≡lateral touching force parallel to the x-axis at time t (with opposite sense);

F(y,t)≡lateral touching force parallel to the y-axis at time t (with opposite sense);

F(z,t)≡normal touching force parallel to the z-axis at time t (with opposite sense, compression being positive); and d≡axial distance between the touching point of the lateral forces and the cross-section of the catheter centered about the distal fiber Bragg gratings 50.

The axial distance d and the forces F(x,t), F(y,t) and F(z,t) are depicted in FIG. 3.

Having solved for the normal force F(z,t) and the lateral forces F(x,t) and F(y,t), a normal force Fnorm(t) at time t and a transverse force Ftrans(t) at time t of the touching force vector F may be computed:

$$\text{Fnorm}(t)=F(z,t) \qquad \text{Eqn. (20)}$$

$$F\text{trans}(t)=\text{sqrt}[F(x,t)^2+F(y,t)^2] \qquad \text{Eqn. (21)}$$

An angle γt of incidence of the transverse force Ftrans(t) at time t and relative to the z-axis may be computed from Table I:

TABLE I

| F(x, t) | F(y, t) | γt |
|---|---|---|
| ≥0 | ≥0 | arcsin[F(y, t)/Ftrans(t)] |
| <0 | ≥0 | Π − arcsin[F(y, t)/Ftrans(t)] |
| <0 | <0 | Π + arcsin[F(y, t)/Ftrans(t)] |
| ≥0 | <0 | 2*Π − arcsin[F(y, t)/Ftrans(t)] |

Many of the values employed in Eqns. (8) to (18) are related to the material properties of the deformable body or optical fiber sensors, such as the Bragg wavelengths, thermal expansion coefficients and elastic moduli of the deformable body. Other values, such as the distances between the optical fiber sensors and the external surface of the deformable body may be subject to variations as a consequence of the manufacturing process employed.

To ensure the accuracy of the computed force vector, specific information (e.g. calibration and geometric information) for each deformable body may be stored in the storage device 177. Generally, the information may take the form of a data file that is input to the storage device 177. For example, storage device 177 may comprise a memory chip associated with the manipulator 20 in which such information is stored, or a bar code or a RFID tag located on the manipulator arm 20 or the packaging for the manipulator arm 20. Alternatively, data specific to the manipulator arm may be uploaded to storage device 177 from an external computer via an item of removable storage (e.g., CD) or via a secure download from the manufacturer's website.

The information specific to each deformable body may be obtained during a calibration step, conducted during manufacture of the deformable body, by subjecting the manipulator arm 20 to a series of known forces. In this case, the foregoing equations may be collapsed so the normal and transverse forces may be computed directly from a force-to-wavelength conversion matrix:

$$F(t)=K(\lambda(t)-\lambda_0) \qquad \text{Eqn. (22)}$$

where: F(t) is the vector of forces [F(x,t), F(y,t), F(z,t)];

λ(t) is the vector of wavelengths [λ(1,t), λ(2,t), λ(3,t)] measured for the individual sensors at time t;

$\lambda_0$ is the reference vector of wavelengths [λ(1,r), λ(2,r), λ(3,r)] measured for the individual sensors at time r with zero applied force; and K is a matrix computed when the deformable body is subjected to the series of known forces.

During the calibration step of manufacture, the deformable body may be subjected to the following forces in series: (1) a purely axial force of known magnitude Fa; (2) a lateral force of known magnitude Fb applied perpendicular to the axial force Fa; and (3) a lateral force of known magnitude Fc applied perpendicular to the axial force Fa and 190 degrees to the orientation of force Fb. When all of the forces Fa, Fb and Fc, and wavelength vectors λ(t) and $\lambda_0$ are known, the force-to-strain conversion matrix K may be computed as:

$$K=F(\lambda(t)-\lambda_0)^{-1} \qquad \text{Eqn. (23)}$$

or:

$$\begin{bmatrix} Fa & 0 & 0 \\ 0 & Fb & 0 \\ 0 & 0 & Fc \end{bmatrix} \begin{bmatrix} (\lambda 1a-\lambda^0 1) & (\lambda 1b-\lambda^0 1) & (\lambda 1c-\lambda^0 1) \\ (\lambda 2a-\lambda^0 2) & (\lambda 2b-\lambda^0 2) & (\lambda 2c-\lambda^0 2) \\ (\lambda 3a-\lambda^0 3) & (\lambda 3b-\lambda^0 3) & (\lambda 3c-\lambda^0 3) \end{bmatrix}^{-1} = \begin{bmatrix} k11 & k12 & k13 \\ k21 & k22 & k23 \\ k31 & k32 & k33 \end{bmatrix} \qquad \text{Eqn. (24)}$$

The force-to-strain conversion matrix K may be stored in the storage device 177 for access by the microprocessor 176 and associated with the corresponding manipulator arm, as described herein above. Once matrix K is provided for a given manipulator arm, the normal force Fnorm(t), transverse force and angle of application of the transverse force may be computed as described above and using Table I.

The values for the normal force, transverse force and angle of application of the transverse force Ftrans(t), computed as described above, may be output as numerical values, for example to a display monitor. In addition, a graphic including a variable size or colored arrow may be output pointing at a position on the circumference of a circle to visualize the magnitude and direction of the transverse force applied to the distal extremity of the deformable body. By monitoring an active display, the operator may continuously obtain feedback concerning the contact forces applied to the distal extremity of the deformable body.

References to relative terms such as upper and lower, front and back, left and right, or the like, are intended for convenience of description and are not contemplated to limit the invention, or its components, to any specific orientation. All dimensions depicted in the figures may vary with a potential design and the intended use of a specific embodiment of this invention without departing from the scope thereof.

Each of the additional figures and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the present invention, it is expressly intended that the provisions of Section 112, sixth paragraph of 35 U.S.C. are not to be invoked unless the specific terms "means for" or "step for" are recited in the subject claim.

What is claimed is:

1. A shape sensing manipulator, comprising:

a proximal portion;

a flexing portion distal to the proximal portion;

a distal portion extending from and distal to the flexing portion, the distal portion including a yoke portion coupled to the flexing portion, the distal portion including a rigid section;

a steering mechanism extending distally through the flexing portion and terminating at the yoke portion, the steering mechanism coupled to the yoke portion and configured to flex the flexing portion, wherein the distal portion is isolated from flexure of the flexing portion; and a plurality of fiber optics extending through at least the flexing portion, and terminating in the distal portion, the plurality of fiber optics having uniform rotational disposition about a longitudinal axis of the flexing portion, wherein one or more of the plurality of fiber optics includes a plurality of optical fiber strain sensors, at least one first optical fiber strain sensor of the plurality of optical fiber strain sensors disposed in the flexing portion and configured to sense a shape of at least the flexing portion of the manipulator and at least one second optical fiber strain sensor of the plurality of optical fiber strain sensors disposed in the distal portion.

2. The shape sensing manipulator of claim 1, wherein the plurality of optical fiber strain sensors are fiber Bragg gratings disposed along a length of the flexing portion, and each of the plurality of fiber Bragg gratings is configured to sense a localized shape of the flexing portion.

3. The shape sensing manipulator of claim 1, wherein the one or more of the plurality of fiber optics further includes at least one temperature sensor operatively coupled with the distal portion; and wherein the at least one temperature sensor includes a fiber Bragg grating.

4. The shape sensing manipulator of claim 1 further including:

an electromagnetic source adapted for connection with the plurality of fiber optics, the electromagnetic source configured to deliver electromagnetic radiation to the plurality of optical fiber strain sensors;

a receiver operatively coupled to the plurality of fiber optics for detection of electromagnetic radiation reflected from the plurality of optical fiber strain sensors; and a microprocessor operatively coupled with the electromagnetic source and the receiver, the microprocessor configured to control the electromagnetic source and the receiver.

5. The shape sensing manipulator of claim 4, wherein the plurality of optical fiber strain sensors are fiber Bragg gratings, and each of the fiber Bragg gratings is configured to reflect a distinct central wavelength in an unstrained state; and the microprocessor is further configured to analyze the electromagnetic radiation received by the receiver and to identify the state of each of the fiber Bragg gratings along each of the plurality of fiber optics by wavelength division multiplexing.

6. The shape sensing manipulator of claim 4, wherein the receiver is an optical frequency-domain reflectometer, and the electromagnetic source is further configured to operate as a swept wavelength source.

7. The shape sensing manipulator of claim 6, wherein the plurality of optical fiber strain sensors are fiber Bragg gratings, and each of the fiber Bragg gratings is spaced a unique distance from a reflector operatively coupled with one of the plurality of fiber optics, each of the fiber Bragg gratings combines with the reflector to form an interferometer with a unique optical-path difference, the interferometers is configured in response to interrogation from the electromagnetic source to modulate reflected components of each of the fiber Bragg gratings with a unique frequency that is directly dependent on the path difference.

8. The shape sensing manipulator of claim 1, wherein the one or more plurality of fiber optics are operatively coupled to the yoke portion.

9. A position sensing manipulator, comprising:

a base;

a flexing portion extending from the base and defining a longitudinal axis, wherein the flexing portion comprises an elongate flexible body between the base and a distal portion;

the distal portion extending from and distal to the flexing portion, the distal portion including a rigid section;

a plurality of fiber Bragg gratings, at least one first fiber Bragg grating of the plurality of fiber Bragg gratings disposed in the flexing portion and at least one second fiber Bragg grating of the plurality of fiber Bragg gratings disposed in the distal portion, the plurality of fiber Bragg gratings configured to determine a shape of the flexing portion and a location of the distal portion, the distal portion including a yoke portion coupled to the flexing portion; and a steering mechanism extending distally through the flexing portion and terminating at the yoke portion, the steering mechanism coupled to the yoke portion and configured to flex the flexing portion, wherein the distal portion is isolated from flexure of the flexing portion, wherein the plurality of fiber Bragg gratings are operatively coupled to a plurality of fiber optics routed along a length of the flexing portion, wherein the plurality of fiber optics are parallel to the longitudinal axis of the flexing portion and having uniform rotational disposition about the longitudinal axis of the flexing portion so that the plurality of fiber Bragg gratings are positioned into groups of three or more fiber Bragg gratings substantially centered at a corresponding location along the longitudinal axis.

10. The position sensing manipulator of claim 9, further including at least one temperature sensor operatively coupled with the distal portion.

11. The position sensing manipulator of claim 10, wherein the at least one temperature sensor includes a fiber Bragg grating.

12. The position sensing manipulator of claim 9, wherein the plurality of fiber Bragg gratings include a spacing configured to facilitate shape determination of the flexing portion.

13. The position sensing manipulator of claim 9, further including an electromagnetic source adapted for connection with a distal end of one or more of the plurality of fiber optics, the electromagnetic source configured to deliver electromagnetic radiation to the plurality of fiber Bragg gratings;

a receiver operatively coupled to the one or more of the plurality of fiber optics for detection of electromagnetic radiation reflected from the plurality of fiber Bragg gratings; and a microprocessor operatively coupled with the electromagnetic source and the receiver, the microprocessor configured to control the electromagnetic source and the receiver.

14. The position sensing manipulator of claim 13, wherein each of the fiber Bragg gratings is configured to reflect a distinct central wavelength in an unstrained state; and the microprocessor is further configured to analyze the electromagnetic radiation received by the receiver and to identify the state of each of the fiber Bragg gratings by wavelength division multiplexing.

15. The position sensing manipulator of claim 14, wherein the receiver is an optical frequency-domain reflectometer, and the electromagnetic source is further configured to operate as a swept wavelength source.

* * * * *